(12) United States Patent
Shultz et al.

(10) Patent No.: US 12,269,843 B2
(45) Date of Patent: *Apr. 8, 2025

(54) REFOLDING PROTEINS USING A CHEMICALLY CONTROLLED REDOX STATE

(71) Applicant: AMGEN INC., Thousand Oaks, CA (US)

(72) Inventors: Joseph Edward Shultz, Santa Rosa Valley, CA (US); Roger Hart, Loveland, CO (US); Ronald Nixon Keener, III, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/889,559

(22) Filed: Feb. 6, 2018

(65) Prior Publication Data

US 2019/0055281 A1    Feb. 21, 2019

Related U.S. Application Data

(60) Continuation of application No. 15/422,327, filed on Feb. 1, 2017, now Pat. No. 9,856,287, and a continuation of application No. 14/793,590, filed on Jul. 7, 2015, which is a continuation of application No. 14/611,037, filed on Jan. 30, 2015, which is a division of application No. 12/820,087, filed on Jun. 21, 2010, now Pat. No. 8,952,138.

(60) Provisional application No. 61/219,257, filed on Jun. 22, 2009.

(51) Int. Cl.
| | |
|---|---|
| *A61K 39/395* | (2006.01) |
| *C07K 1/113* | (2006.01) |
| *C07K 1/14* | (2006.01) |
| *C07K 14/00* | (2006.01) |
| *C07K 16/00* | (2006.01) |

(52) U.S. Cl.
CPC .......... *C07K 1/1136* (2013.01); *C07K 1/1133* (2013.01); *C07K 1/14* (2013.01); *C07K 14/00* (2013.01); *C07K 16/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,237,224 A | 12/1980 | Cohen et al. |
| 4,468,454 A | 8/1984 | Cohen et al. |
| 4,468,464 A | 8/1984 | Cohen et al. |
| 4,572,798 A | 2/1986 | Koths et al. |
| 4,740,470 A | 4/1988 | Cohen et al. |
| 4,810,643 A | 3/1989 | Souza |
| 4,977,248 A | 12/1990 | Creighton |
| 5,466,377 A | 11/1995 | Grandics et al. |
| 5,663,304 A | 9/1997 | Builder et al. |
| 5,849,883 A | 12/1998 | Boone et al. |
| 5,922,846 A | 7/1999 | Cerletti et al. |
| 5,986,070 A | 11/1999 | Collins et al. |
| 6,180,391 B1 | 1/2001 | Brown |
| 6,322,779 B1 | 11/2001 | Halenbeck et al. |
| 6,660,843 B1 | 12/2003 | Feige et al. |
| 6,808,902 B1 | 10/2004 | Treuheit et al. |
| 6,972,327 B1 | 12/2005 | Madani et al. |
| 7,083,948 B1 | 8/2006 | Sassenfeld et al. |
| 7,118,884 B1 | 10/2006 | Curless et al. |
| 7,138,370 B2 | 11/2006 | Oliner et al. |
| 7,384,765 B1 | 6/2008 | Follstad et al. |
| 7,427,659 B2 | 9/2008 | Shukla et al. |
| 7,435,804 B2 | 10/2008 | Kordyum et al. |
| 7,442,778 B2 | 10/2008 | Gegg et al. |
| 7,511,012 B2 | 3/2009 | Han et al. |
| 7,662,930 B2 | 2/2010 | Zhou |
| 7,723,490 B2 | 5/2010 | Treuheit et al. |
| 7,735,525 B2 | 6/2010 | Lunsford et al. |
| 7,781,395 B2 | 8/2010 | Senczuk et al. |
| 8,191,566 B2 | 6/2012 | Donahue |
| 8,273,707 B2 | 9/2012 | Senczuk et al. |
| 8,629,250 B2 | 1/2014 | Sasu et al. |
| 8,906,648 B2 | 12/2014 | Butler et al. |
| 8,940,878 B2 | 1/2015 | Shultz et al. |
| 8,952,138 B2 | 2/2015 | Shultz et al. |
| 9,090,684 B2 | 7/2015 | Borras et al. |
| 9,200,030 B2 | 12/2015 | Pizarro et al. |

(Continued)

FOREIGN PATENT DOCUMENTS

| | | |
|---|---|---|
| CA | 2614820 A1 | 1/2007 |
| CN | 1295580 A | 5/2001 |

(Continued)

OTHER PUBLICATIONS

Burks et al.; "Rapid, High-Yield Recovery of a Recombinant Digoxin Binding Single Chain Fv from *Escherichia coli*", Biotechnol. Prog., 1995, 11, pp. 112-114.

Ferré et al.; "A novel system for continuous protein refolding and on-line capture by expanded bed adsorption", Protein Science, 2005, 14, pp. 2141-2153.

GE Handbook, Ion Exchange Chromatography & Chromatofocusing—Principles and Methods, 2004, 188 pages.

Hahm, et al.; "Refolding and Purification of Yeast Carboxypeptidase Y Expressed as Inclusion Bodies in *Escherichia coli*"; Protein Expression and Purification, 2001, 22, pp. 101-107.

(Continued)

*Primary Examiner* — Yunsoo Kim
(74) *Attorney, Agent, or Firm* — Ruggiero McAllister & McMahon LLC

(57) ABSTRACT

A method of refolding proteins expressed in non-mammalian cells present in concentrations of 2.0 g/L or higher is disclosed. The method comprises identifying the thiol pair ratio and the redox buffer strength to achieve conditions under which efficient folding at concentrations of 2.0 g/L or higher is achieved and can be employed over a range of volumes, including commercial scale.

9 Claims, 8 Drawing Sheets

(56) References Cited

U.S. PATENT DOCUMENTS

| | | | |
|---|---|---|---|
| 9,418,416 | B2 | 8/2016 | Milne et al. |
| 9,540,429 | B2 | 1/2017 | Scher et al. |
| 9,632,095 | B2 | 4/2017 | Roberts et al. |
| 9,704,239 | B1 | 7/2017 | Milne et al. |
| 9,815,879 | B2 | 11/2017 | Dietrich et al. |
| 2004/0018586 | A1 | 1/2004 | Rosendahl et al. |
| 2005/0159589 | A1 | 7/2005 | Porekar et al. |
| 2005/0209441 | A1 | 9/2005 | Lile |
| 2006/0172384 | A1 | 8/2006 | Reardon et al. |
| 2006/0228329 | A1 | 10/2006 | Brady et al. |
| 2007/0082362 | A1 | 4/2007 | Jakobsen et al. |
| 2007/0238860 | A1 | 10/2007 | Schlegl |
| 2008/0095775 | A1 | 4/2008 | Lewis et al. |
| 2008/0096370 | A1 | 4/2008 | Anderson et al. |
| 2008/0171857 | A1 | 7/2008 | Komath et al. |
| 2008/0214795 | A1 | 9/2008 | Ramanan et al. |
| 2008/0260674 | A1 | 10/2008 | Dietrich et al. |
| 2008/0260684 | A1 | 10/2008 | Dietrich et al. |
| 2010/0267936 | A1 | 10/2010 | Treuheit et al. |
| 2015/0315232 | A1 | 11/2015 | Shultz et al. |
| 2015/0329586 | A1 | 11/2015 | Shultz et al. |

FOREIGN PATENT DOCUMENTS

| | | |
|---|---|---|
| DE | 10-2005-033250 A1 | 1/2007 |
| DE | 2005/033250 A1 | 1/2007 |
| EP | 0309569 A1 | 4/1989 |
| EP | 0 336 631 B1 | 10/1989 |
| EP | 0 433 225 A1 | 6/1991 |
| EP | 0 657 466 A1 | 6/1995 |
| EP | 1021528 A1 | 7/2000 |
| EP | 1310559 A1 | 5/2003 |
| EP | 1 449 848 A1 | 8/2004 |
| EP | 1630173 A2 | 3/2006 |
| EP | 1 845 103 A1 | 10/2007 |
| WO | WO 84/03711 | 9/1984 |
| WO | WO 88/08003 | 10/1988 |
| WO | WO 89/10932 | 11/1989 |
| WO | 1992/004382 A1 | 3/1992 |
| WO | WO93/18136 | 9/1993 |
| WO | 95/32216 A1 | 11/1995 |
| WO | 1995032216 | 11/1995 |
| WO | WO 96/40912 | 12/1996 |
| WO | 9727219 A1 | 1/1997 |
| WO | 1997/028272 A1 | 8/1997 |
| WO | 1999/042486 A1 | 8/1999 |
| WO | 1999060119 | 11/1999 |
| WO | 1999060120 | 11/1999 |
| WO | 2001/007477 A1 | 2/2001 |
| WO | WO 0 1/87925 | 11/2001 |
| WO | 2002/020762 A3 | 8/2002 |
| WO | 2002068455 | 9/2002 |
| WO | WO 2004/001056 | 12/2003 |
| WO | 2005089102 A2 | 9/2005 |
| WO | 2006023782 A2 | 3/2006 |
| WO | 2006/036834 A2 | 4/2006 |
| WO | 2006047340 A2 | 5/2006 |
| WO | 2006047340 | 6/2006 |
| WO | WO 2006/097944 | 9/2006 |
| WO | WO 2007/009950 | 1/2007 |
| WO | 2007022070 A2 | 2/2007 |
| WO | 2004/058988 A3 | 11/2007 |
| WO | 2008097829 A2 | 8/2008 |
| WO | WO 2008/096370 | 8/2008 |
| WO | 2009/023270 A1 | 2/2009 |
| WO | 2009107129 A1 | 9/2009 |
| WO | WO2011/005488 A1 | 1/2011 |
| WO | WO2014/144903 A1 | 9/2014 |

OTHER PUBLICATIONS

Hanes, et al.; "Ribosome display efficiently selects and evolves high-affinity antibodies in vitro from immune libraries", Proc. Natl. Acad. Sci. USA, Nov. 1998, vol. 95, pp. 14130-14135.

Hievehan, et al.; "Oxidative Renaturation of Lysozyme at High Concentrations"; Biotechnology and Bioengineering, vol. 54, No. 3, May 5, 1997, pp. 221-230.

Hiremath, et al.; "Expression and Purification of Recombinant hRPABC25, hRPABC17, and hRPABC14.4, Three Essential Subunits of Human RNA Polymerases I, II, and III", Protein Expression and Purification, 1998, 13, pp. 198-204, Article No. PT980889.

Holzinger, et al.; "Single-Step Purification/Solubilization of Recombinant Proteins: Application to Surfactant Protein B", BioTechniques, vol. 20, No. 5, 1996, pp. 804-808.

Johnson et al.; "Refolding, Purification, and Characterization of Human Erythropoietin Binding Protein Produced in *Escherichia coli*", Protein Expression and Purification 7, 1996, Article No. 0014, pp. 104-113.

Pavlinkova, et al.; "Charge-Modified Single Chain Antibody Constructs of Monoclonal Antibody CC49: Generation, Characterization, Pharmacokinetics, and Biodistribution Analysis", Nuclear Medicine & Biology, vol. 26, 1999, pp. 27-34.

Ronnmark, et al., "Construction and characterization of affibody-Fc chimeras produced in *Escherichia coli*"; Journal of Immunological Methods, 2002, 261, pp. 199-211.

Extended European Search Report dated Jun. 19, 2018 from corresponding European Patent Application No. 18167168.6, 13 pages.

Creighton, Thomas E.; "Renaturation of the Reduced Boving Pancreatic Trypsin Inhibitor"; J. Mol. Biol., 1974, 87, pp. 563-577.

Amgen s Responses to Defendants Invalidity Contentions, Apr. 19, 2019.

Appendices to Amgen s Responses, Apr. 19, 2019.

Appx 1A Response to Vallejo 287 , Apr. 19, 2019.

Appx 1B Response to Schlegl 287 , Apr. 19, 2019.

Appx 1C Response to Hevehan 287 , Apr. 19, 2019.

Appx 1D Response to Ruddon 287 , Apr. 19, 2019.

Appx 1E Response to Omnibus 287 , Apr. 19, 2019.

Appx 2A Response to Hevehan 138 , Apr. 19, 2019.

Appx 2B Response to Collins 138 , Apr. 19, 2019.

Appx 2C Response to Lewis 138 , Apr. 19, 2019.

Appx 2D Response to Schlegl 138 , Apr. 19, 2019.

Appx 2E Response to Omnibus 138 , Apr. 19, 2019.

Appx 3A Response to Ferre 878 , Apr. 19, 2019.

Appx 3B Response to Komath 878 , Apr. 19, 2019.

Appx 3C Response to Halenbeck 878 , Apr. 19, 2019.

Appx 3D Response to Dasari 878 , Apr. 19, 2019.

Appx 4A Response to Ferre 997 , Apr. 19, 2019.

Appx 4B Response to Komath 997 , Apr. 19, 2019.

Appx 4C Response to Hahm 997 , Apr. 19, 2019.

Appx 4D Response to Dietrich 997 , Apr. 19, 2019.

Appx 4E Response to Halenbeck 997 , Apr. 19, 2019.

Appx 4F Response to Dasari 997 , Apr. 19, 2019.

Declaration of Zhaohui Sunny Zhou, Apr. 15, 2019.

Mar. 29, 2019 Defendants Invalidity Contentions Cover Pleading , Mar. 29, 2019.

Amgen s Markman Opening Brief, Apr. 15, 2019.

Declaration of Richard C. Page with Exhibits AG, Apr. 15, 2019.

Declaration of Richard C. Willson with Exhibits AC, Apr. 15, 2019.

Defendants Markman Opening Brief, Apr. 15, 2019.

Ex. 1A Defendants 287 Invalidity Chart Vallejo , Mar. 29, 2019.

Ex. 1B Defendants 287 Invalidity Chart Schlegl , Mar. 29, 2019.

Ex. 1C Defendants 287 Invalidity Chart Hevehan , Mar. 29, 2019.

Ex. 1D Defendants 287 Invalidity Chart Ruddon , Mar. 29, 2019.

Ex. 1E Defendants 287 Invalidity Chart 138 Patent , Mar. 29, 2019.

Ex. 1F Defendants 287 Invalidity Chart Omnibus , Mar. 29, 2019.

Ex. 2A Defendants 138 Invalidity Chart Hevehan , Mar. 29, 2019.

Ex. 2B Defendants 138 Invalidity Chart Collins , Mar. 29, 2019.

Ex. 2C Defendants 138 Invalidity Chart Lewis , Mar. 29, 2019.

Ex. 2D Defendants 138 Invalidity Chart Schlegl , Mar. 29, 2019.

Ex. 2E Defendants 138 Invalidity Chart Omnibus , Mar. 29, 2019.

Ex. 3A Defendants 878 Invalidity Chart Ferre , Mar. 29, 2019.

Ex. 3B Defendants 878 Invalidity Chart Komath , Mar. 29, 2019.

Ex. 3C Defendants 878 Invalidity Chart Halenbeck , Mar. 29, 2019.

Ex. 3D Defendants 878 Invalidity Chart Dasari , Mar. 29, 2019.

Ex. 4A Defendants 997 Invalidity Chart Ferre , Mar. 29, 2019.

Ex. 4B Defendants 997 Invalidity Chart Komath , Mar. 29, 2019.

Ex. 4C Defendants 997 Invalidity Chart Hahm , Mar. 29, 2019.

(56) References Cited

OTHER PUBLICATIONS

Ex. 4D Defendants 997 Invalidity Chart Dietrich , Mar. 29, 2019.
Ex. 4E Defendants 997 Invalidity Chart Halenbeck , Mar. 29, 2019.
Ex. 4F Defendants 997 Invalidity Chart Dasari , Mar. 29, 2019.
Final Initial Invalidity Contentions Jan. 11, 2019 Signed, Jan. 11, 2019.
IPR2016-01542 Record of Oral Hearing, Held Dec. 13, 2017.
IPR2016-01542 Second Declaration of Dr. Anne Robinson.
IPR2016-01542 Sep. 26, 2017, Deposition Transcript of Anne S. Robinson, Ph.D.
IPR2016-01542, Apotex Request for Rehearing, Mar. 16, 2018.
Jun. 13, 2017 Email to Petitioners Counsel [filed in support of Amgens Motion to Exclude, attached as an exhibit to Amgens Motion to Exclude, filed in support of Amgens Opposition to Apotexs Motion to Exclude, and attached as an exhibit to Amgens Motion to Submit Supplemental Information].
Kuwajima, K., "The molten globule state of a-lactalbumin," FASEB J, (1996) 10:102-109.
Majidzadeh et al, "Human Tissue Plasminogen Activator Expression in *Escherichia coli* using Cytoplasmic and Periplasmic Cumulative Power," Avicenna Journal of Medical Biotechnology, (2010) 2:131-136.
Pan et al., "Engineering batch and pulse refolding with transition of aggregation kinetics: An investigation using green fluorescent protein (GFP)," Chemical Engineering Science, 131 (2015) 91-100.
Roberts, "Non-Native Protein Aggregation Kinetics" Biotechnology Bioengineering, (2007) 98(5)927-938.
Slangen et al., "Use of Mass Spectrometry to Rapidly Characterize the Heterogeneity of Bovine a-Lactalbumin," J. Agric. Food Chem., vol. 47, pp. 4549-4556 (1999).
Thatcher, D., "Recovery of therapeutic proteins from inclusion bodies: problems and process strategies," Biochemical Society Transactions (1990)18(2)234-235.
Web of Science database results of Aug. 21, 2017 re Buswell et al., "A New Kinetic Scheme for Lysozyme Refolding and Aggregation," Biotechnology and Bioengineering, 83(5), pp. 567-577 (Sep. 5, 2003).
Amgen Inc. and Amgen Manufacturing, Limited"s Preliminary Proposed Claim Constructions, C.A. No. 1:18-cv-03347-CCC-MF (D.N.J. Feb. 27, 2019).
Appendix 3-B: Response to Adellos Invalidity Contentions Against the 878 Patent (Komath).
Apr. 22, 2016 Amgens Reply Claim Construction Brief, in *Amgen Inc. et al.* v. *Sandoz Inc. et al.*, 14-cv-04741-RS (N.D. Cal.).
Aug. 4, 2016 Order Construing Claims, in *Amgen Inc. et al.* v. *Sandoz Inc. et al.*, 14-cv-04741-RS (N.D. Cal.).
Bruce Alberts et al., Molecular Biology of the Cell, 4th edition, New York: Garland Science (2002) From RNA to Protein, available at https://www.ncbi.nlm.nih.gov/books/NBK26829/.
C.R. Dean and O.P. Ward, "The Use of EDTA or Polymyxin with Lysozyme for the Recovery of Intracellular Products from *Escherichia coli*," Biotechnology Techniques, 6:133-138 (1992).
Chaozhan Wang et al., "Solubilization and Refolding with Simultaneous Purification of Recombinant Human Stem Cell Factor," Appl. Biochem. Biotechnol., 144:181-189 (2008).
Chinnaswamy Tiruppathi et al. "Ioslation and Characterization of a Cell Surface Albumin-Binding Protein from Vascular Endothelial Cells" Proc. Natl. Acad. Sci. USA, 93:250-254 (1996).
Christopher Hill et al., "The Structure of Granulocyte-ColonyStimulating Factor and its Relationship to Other Growth Factors," Proc. Natl. Acad. Sci USA, 90: 5167-5171 (1993).
David N. Garboczi et al. "Mitochondrial ATP Synthase: Overexpression in *Escherichia coli* of a Rat Liver 0 Subunit Peptide and Its Interaction with Adenine Nucleotides" Journal of Biological Chemistry, 263: 15694-15698 (1988).
David Smith and Sheena Radford, "Role of the Single Disulphide Bond of p2-Microglobulm in Amyloidosis In Vitro," Protein Science, 10:1775-1784 (2001).
IPR2019-00791 Patent Owners Preliminary Response (878), Jun. 14, 2019.

IPR2019-00791 , *Kashiv Biosciences* v *Amgen*, Petition for Inter Partes Review, Mar. 7, 2019.
Jens Tyedmers et al., "Cellular strategies for controlling protein aggregation," Nature Reviews (2010).
Krister Holmberg et al., Surfactants and Polymers in Aqueous Solution, John Wiley Sons, Ltd., Chapter 1 (2002).
Merriam-Webster"s Collegiate Dictionary (2009).
Merriam-Webster"s Medical Desk Dictionary (2006).
Nov. 13, 2017 Amgens Opposition to Sandozs Motion for Summary Judgement on Damages, in *Amgen Inc. et al.* v. *Sandoz Inc. et al.*, 14-cv-04741-RS (N.D. Cal.).
Paul Wingfield, "Protein Precipitation Using Ammonium Sulfate," Curr. Protoc. Protein Sci., 13: A.3F.1-A.3F.8. (2001) (Author Manuscript).
Robert M. Kennedy, "Expanded Bed Adsorption Chromatography," in Current Protocols in Protein Science, John Wiley Sons, Inc. (2005).
Serena Webb et al., "A New Mechanism for Decreasing Aggregation of Recombinant Human Interferon-y by a Surfactant: Slowed Dissolution of Lyophilized Formulations in a Solution Containing 0.03% Polysorbate 20," Journal of Pharmaceutical Sciences, 91:543-558 (2002).
Susanne Gulich, "Engineering of Proteinaceous Ligands for Improved Performance in Affinity Chromatography Applications," Department of Biotechnology, Royal Institute of Technology (2002) pt1.
Susanne Gulich, "Engineering of Proteinaceous Ligands for Improved Performance in Affinity Chromatography Applications," Department of Biotechnology, Royal Institute of Technology (2002) pt2.
Sydney O. Ugwu and Shireesh P. Apte, "The Effect of Buffers on Protein Conformational Stability," Pharmaceutical Technology, 28:86-113 (2004).
Sytske Welling-Wester et al., "Detergent Extraction of Herpes Simplex Virus Type 1 Glycoprotein D by Zwitterionic and NonIonic Detergents and Purification by Ion-Exchange High Performance Liquid Chromatography," Journal of Chromatography A, 816:29-37 (1998).
Tuula Lindholm, et al., "Polysorbate 20 as a drug release regulator in ethyl cellulose film coatings," J. Pharm. Pharmacol., 38:686688 (1986).
U.S. Appl. No. 12/822,990, filed Aug. 28, 2012 NonFinal Rejection.
U.S. Appl. No. 12/822,990, filed Jan. 25, 2013 Amendment Response to Non-Final Rejection.
U.S. Appl. No. 12/822,990, filed Jun. 6, 2014 Non-Final Rejection.
U.S. Appl. No. 12/822,990, filed Sep. 9, 2013 Final Rejection.
"Glutathione" in the Merck Index, 12th Ed., pp. 4483-4484 (Merck Research Laboratories 1996).
Archer, D. et al., "Hen Egg White Lysozyme Expressed in, and Secreted from, Aspergillus Niger is Correctly Processed and Folded," Bio/Technology 8:741-745 (Aug. 1990).
Atassi, M.Z., Chemical Strategy for Studying the Antigenic Structures of Disulfide-Containing Proteins: Hen Egg-White.
Excerpts of U.S. Pat. No. 9,856,287 File History.
Gilbert, H., "Molecular and Cellular Aspects of Thiol-Disulfide Exchange," in Advances in Enzymology and Related Areas of Molecular Biology, ed. Alton Meister, vol. 63, pp. 69-172 (John Wiley Sons 1990).
Gilbert, H., "Thiol/Disulfide Exchange Equilibria and Disulfide Bond Stability," in Methods in Enzymology, ed. Lester Packer, vol. 251, pp. 8-28 (Academic Press 1995).
Horton, R. et al., Principles of Biochemistry ( Pearson Education, 4th ed., 2006).
IPR2019-00971 *Kabi* v *Amgen* (287) Petition for Inter Partes Review, Apr. 14, 2019.
IPR2019-01183 Curriculum Vitae of Professor Paul A. Dalby, Ph.D.
IPR2019-01183 Declaration of Professor Paul A. Dalby, Ph.D.
Keire, D. et al., "Kinetics and Equilibria of Thiol/Disulfide Interchange Reactions of Selected Biological Thiols and Related Molecules with Oxidized Glutathione," J. Org. Chem. 57(1):123-127 (1992).
Middleberg, A., "Preparative protein folding," TRENDS in Biotechnology 20(10):437-443 (Oct. 2002).
Patent Owners Preliminary Response Under 37 C.F.R. § 42.207, dated Jan. 23, 2019.

(56) References Cited

OTHER PUBLICATIONS

Peptides Guide, "What are Proteins" accessed at http: //www.peptidesguide. com/proteins. html.
Ryan, R. et al., "Structure-Function Relationships of Gonadotropins," in Recent Progress in Hormone Research, vol. 43, pp. 383-429 (Academic Press 1987).
Schafer, F. Buettner, G., "Redox Environment of the Cell as Viewed Through the Redox State of the Glutathione Disulfide/Glutathione Couple," Free Radical Biology Medicine 30(11):1191-1212 (Jun. 2001).
Wetlaufer, D. et al., "The oxidative folding of proteins by disulfide plus thiol does not correlate with redox potential," Protein Engineering 1(2):141-146 (1987).
Xie, Y. et al., "Recombinant Human Retinol-Binding Protein Refolding, Native Disulfide Formation, and Characterization," Protein Expression and Purification 14:31-37 (1998).
Information Disclosure Statement, U.S. Appl. No. 12/820,087 (now U.S. Pat. No. 8,952,138), filed Sep. 20, 2012.
Acknowledgement of consideration of references, U.S. Appl. No. 12/820,087 (now U.S. Pat. No. 8,952,138), Jan. 9, 2012.
Information Disclosure Statement, U.S. Appl. No. 12/820,087 (now U.S. Pat. No. 8,952,138), filed Oct. 20, 2010.
Information Disclosure Statement, U.S. Appl. No. 12/820,087 (now U.S. Pat. No. 8,952,138), filed Sep. 23, 2010.
IPR2016-01542 Patent Owners First Amended Exhibit List.
IPR2016-01542 Petitioners Oral Argument Demonstratives.
*Amgen Inc. et al.* v. *Adello Biologics LLC*, Case No. 2:18-cv-03347 (D.N.J.), DE1 (Amgens Complaint).
*Amgen Inc. et al.* v. *Adello Biologics LLC*, Case No. 2:18-cv-03347 (D.N.J.), DE50 (Amgens Amended Complaint).
*Amgen Inc. et al.* v. *Adello Biologics LLC*, Case No. 2:18-cv-03347 (D.N.J.), DE54 (Defendant Adello Biologics, LLCs Answer, Defenses and Counterclaims to Plaintiffs First Amended Complaint).
*Amgen Inc. et al.* v. *Adello Biologics LLC*, Case No. 2:18-cv-03347 (D.N.J.), DE57 (Amneal Pharmaceuticals, Inc. Proof of Service).
*Amgen Inc. et al.* v. *Adello Biologics LLC*, Case No. 2:18-cv-03347 (D.N.J.), DE58 (Amneal Pharmaceuticals, LLC Proof of Service).
*Amgen Inc. et al.* v. *Adello Biologics LLC*, Case No. 2:18-cv-03347 (D.N.J.), DE59 (Miller Appearance for Amneal Pharmaceuticals, LLC and Amneal Pharmaceuticals, Inc.).
*Amgen Inc. et al.* v. *Adello Biologics LLC*, Case No. 2:18-cv-03347 (D.N.J.), DE60 (Gabay Appearance for Amneal Pharmaceuticals, LLC and Amneal Pharmaceuticals, Inc.).
*Amgen Inc. et al.* v. *Adello Biologics LLC*, Case No. 2:18-cv-03347 (D.N.J.), DE70-1 (Brief in Support of Motion to Dismiss).
*Amgen Inc.* v. *Apotex Inc.*, Appeal No. 17-1010 (Fed. Cir.), DE 423 (Joint Appendix vol. III of III).
https://embryology.med.unsw.edu.au/embryology/index.php/Human_C horionic_Gonadotropin.
PGR2019-00001 Table of categorized claims for U.S. Pat. No. 9,856,287.
United States Patent and Trademark Office Before the Patent Trial and Appeals Board. (Sep. 11, 2019)—Decision Granting Institution of Inter Partes Review of U.S. Pat. No. 8,940,878 B2, IPR2019-00791, *Kashiv Biosciences, LLC* Petitioner v. *Amgen Inc.*, Patent Owner, pp. 1-34.
United States Patent and Trademark Office Before the Patent Trial and Appeals Board. (Sep. 11, 2019)—Decision Granting Institution of Inter Partes Review of U.S. Pat. No. 9,643,797, IPR2019-00791, *Kashiv Biosciences, LLC* Petitioner v. *Amgen Inc.*, Patent Owner, pp. 1-36.
United States Patent and Trademark Office Before the Patent Trial and Appeals Board. (Sep. 11, 2019)—Patent Owner's Preliminary Response, Case IPR2019-01183, U.S. Pat. No. 9,643,997, *Fresenius Kabi USA, LLC and Fresenius Kabi Swissbiosim GmbH*, Petitioners v. *Amgen Inc.*, Patent Owner, pp. 1-76.
Enger et al "Concepts in Biology" 10th edition, 2003, McGraw-Hill Publishing.
Paper #60, Final Written Decision, entered Feb. 15, 2018, *Apotex Inc. and Apotex Corp.*, v. *Amgen Inc. and Amgen Manufacturing Limited*, Case IPR2016-01542, U.S. Pat. No. 8,952,138 B2, 49 pages.
Rogl, H. et al. "Refolding of *Escherichia coli* Produced Membrane Protein Inclusion Bodies Immobilised by Nickel Chelating Chromatography." FEBS Letters 432: 21-26 (1998).
Li, Jing-Jing et al."Immobilized fl-cyclodextrin Polymer Coupled to Agarose Gel Properly Refolding Recombinant *Staphylococcus aureus* Elongation Factor-G in Combination with Detergent Micelle" Protein Expression and Purification 45: 72-79 (2006).
Nian, Rui et al."Chaperone-Assisted col. Refolding of Gloshedobin with the Use of Refolding Cocktail", J. of Chromatography A 1214: 47-58 (2008).
Ng et al. "Regeneration Studies of Anion-Exchange Chromatography Resins," BioP'ocess International (May 2007).
Skrlin, A. et al., "Comparison of the physicochemical properties of a biosimilar filgrastim with those of reference filgrastim." Biologicals. 38:557-566 (2010).
Skrlin. A. et al., "Correlation of liquid chromatographic and biological assay for potency assessment of filgrastim and related impurities," Journal of Pharmaceutical and Biomedical Analysis. 53:262-268 (2010).
*TTAB Adello Biologics LLC, Apotex Inc. and Apotex Corp.* v. *Amgen Inc. and Amgen Manufacturing Limited*, Post Grant Review No. PGR2019-00001, Petition for Post Grant Review of U.S. Pat. No. 9,856,287 dated Oct. 1, 2018, 93 pages.
Fred Regnier, "High Performance Ion-Exchange Chromatography," Methods in Enzymology, 104:170-189 (1984).
IPR2019-00797 Appendix 4-B: Response to Adellos Invalidity Contentions Against the 997 Patent (Komath).
IPR2019-00797 Declaration of Anne S. Robinson, Ph.D.
IPR2019-00797 Declaration of Naz Wehrli.
IPR2019-00797 Declaration of Sayem Osman.
Videotaped Deposition of Anne Skaja Robinson, IPR 2016-01542, United States Patent and Trademark Office Before the Patent and Appeal Board, May 8, 2017, pp. 1-72.
Second Declaration of Richard C. Willson, Ph.D., IPR 2016-01542, United States Patent and Trademark Office before the Patent Trial and Appeal Board, May 22, 2017, pp. 1-65.
Contracting the Protein With a Refold Buffer, Slide, Amgen Exhibit 2018, IPR 2016-01542, pp. 1.
Patent Owner's Response, Case IPR 2016-01542, U.S. Pat. No. 8,952,138, United States Patent and Trademark Office Before the Patent Trial and Appeal Board, May 22, 2017, pp. 1-78.
Patent Owner's Motion to Seal, IPR 2016-01542, Date May 22, 2017, pp. 1-6.
Joint Motion for Entry of Stipulated Protective Order, IPR 2016-01542, U.S. Pat. No. 8,952,138, United States Patent and Trademark Office before the Patent Trial and Appeal Board, May 22, 2017, pp. 1-22.
Benham, et al. Disulfide bonding patterns and protein topologies, Protein Science (1993), 2, 41-54. Cambridge University Press, pp. 1-14.
Wilson, Richard C. Updated Resume, Amgen Exhibit 2053, IPR 2016-01542, pp. 1-7.
Amold L. Demain, Pretti Vaishnav, Production of recombinant proteins by microbes and higher organisms, Biotechnology Advances, 27 (2009) pp. 297-306, https://www.researchgate.net/publication/26270590.
Tatsumi E. et al. Denatured State of Ovalbumin in High Concentrations of Urea as Evaluated by Disulfide Rearrangement Analysis, The Journal of Biological Chemistry, vol. 269, No. 45, Issue of Nov. 11, pp. 28062-28067, 1994.
Radford S. et al., The folding of hen lysozyme involves partially structured intermediates and multiple pathways, Amgen Exhibit 2049, IPR 2016-01542, pp. 1-6.
Finke J., et al. Aggregation Events Occur Prior to Stable Intermediate Formation during Refolding of Interleukin 1β. Biochemistry 2000, 39, 575-583.
Booth D., Instability, unfolding and aggregation of human lysozyme variants underlying amyloid fibrillogenesis, Nature, vol. 385, Feb. 27, 1997, Amgen Exhibit 2047, IPR 2016-01542, pp. 1-7.

(56) References Cited

OTHER PUBLICATIONS

Jiang X., et al. The V122I cardiomyopathy variant of transthyretin increases the velocity of rate-limiting tetramer dissociation, resulting in accelerated amyloidosis, Department of Chemistry and the Skaggs Institute of Chemical Biology, pp. 1-6.
Darby, N. et al., Refolding of Bovine Pancreatic Trypsin Inhibitor via Non-native Disulphide Intermediates, J. Mol. Biol. (1995) 249, 463-477.
Tobacman, L. et al., The Kinetics of Actin Nucleation and Polymerization, The Journal of Biological Chemistry, vol. 258, No. 5, Issue of Mar. 10, pp. 3207-3214, 1983, pp. 1-9.
Ferrone, F., Analysis of Protein Aggregation Kinetics, Methods of Enzymology, vol. 309, Amgen Exhibit 2043, IPR 2016-01542, pp. 1-19.
Matagne, A., The folding process of hen lysozyme: a perspective from the "new view", CMLS, Cell. Mil. Life Sci. 54 (1998) 363-371.
Buswell, M., et al., A New Kinetic Scheme for Lysozyme Refolding and Aggregation Department of Chemical Engineering, University of Cambridge, Pembroke Street, Cambridge CB2 3RA United Kingdom, DOI: 10.1002/bit.10705, Received Nov. 8, 2002; accepted Mar. 3, 2003, Amgen Exhibit 2042, pp. 1-11.
Matthews, R. Pathways of Protein Folding, Department of Chemistry, Pennsylvania State University, University Park, Pennsylvania 16802, Annu. Rev. Biochem. 1993, 62:653-83, Amgen Exhibit 2039, pp. 1-33.
Svensson, M. et al., Conversion of α-lactalbumin to a prtein inducing apoptosis, Department of Microbiology, Immunology, and Glycobiology, Institute of Laboratory Medicine, Lund University, Solvegata 23, S-223, 62 Lund, Sweden, PNAS, Apr. 11, 2000, vol. 97, No. 8, 4221-4226, Amgen Exhibit 2040, pp. 1-6.
Permyakov E. et al., α-lactalbumin: structure and function, FEBS Letters 473 (2000) 260-274, Amgen Exhibit 2038, pp. 1-6.
Ewbank, J. et al., Structural Characterization of the Disulfide Folding Intermediates of Bovine α-Lactalbumin, Biochemistry 1993, 32, 3694-3707, Amgen Exhibit 2036, pp. 1-14.
Georgiou, G., Isolating Inclusion Bodies from Bacteria, In Vivo Protein Deposition, Amgen Exhibit 2034, pp. 1-11.
Darby, N., Feature-blind grammar and dysphasia, Scientific Correspondence, Nature, vol. 344, Apr. 19, 1990, Amgen Exhibit 2035, pp. 1-2.
Maachupalli-Reddy, J. et al., Effect of Inclusion Body Contaminants on the Oxidative Renaturation of Hen Egg White Lysozyme, Biotechnol. Prog. 1997, 13, 144-150, Amgen Exhibit 2033, pp. 1-7.
Chow, Michelle, et al., Refold: An analytical database of protein refolding methods, Science Direct, Protein Expression & Purification, Received Jun. 14, 2005, and in revised form Jul. 19, 2005, available online Aug. 15, 2005, Amgen Exhibit 2032, pp. 1-6.
Eiberle, M., Technical refolding of proteins: Do we have freedom to operate? Biotechnol. J. 2010, 5, 547-559, Amgen Exhibit 2030, pp. 1-13.
Lilie H. et al., Advances in refolding of proteins produced in *E. coli*, Current Opinion in Biotechnology, 1998, 9: 497-501, Amgen Exhibit 2031, pp. 1-5.
Declaration of Anne S. Robinson, Ph.D. in support of defendants' opening claim construction brief, Dated Dec. 11, 2015, Amgen Exhibit 2029, IPR 2016-01542, pp. 1-42, United States District Court Southern District of Florida.
Transcript of Bench Trial Proceedings Before the Honorable James I. Cohn U.S. District Judge, dated Jul. 14, 2016, Fort Lauderdale, Florida, Amgen Exhibit 2028, pp. 1-242.
Padhi D et al., Pharmacological Inhibition of Myostatin and Changes in Lean Body Mass and Lower Extremity Muscle Size in Patients Receiving Anddrogen Deprivation Therapy for Prostate Cancer, JCEM Online, Hot Topics in Translational Endocrinology—Endocrine Research, J Clin Endcrinol Metab, Oct. 2014, 99(10)E1967-1975, ISSN Online 1945-7197, Accepted Jun. 2, 2014, First Published Online Jun. 27, 2014, Amgen Exhibit 2026, pp. 1-9.

Declaration of Roger A. Hart, Ph.D., IPR2016-01542, United States Patent and Trademark Office Before the Patent Trial and Appeal Board, Amgen Exhibit 2021, pp. 1-39.
Defendants' Invalidity Contentions, Case No. 3:14-cv-04741-RS, United States District Court Northern District of California San Francisco Division, pp. 1-186.
Edward R. Barnhart, Physicians' Desk Reference, 46th Ed., Neupogen®, 595-598.
R.L. Basser et al., Adjuvant Treatment of High-Risk Breast Cancer Using Multicycle High-Dose Chemotherapy and Filgrastim-mobilized Peripheral Blood Progenitor Cells, Clin. Cancer Res. 1:715-721 (Jul. 1995).
C.G. Begley et al., G-CSF Mobilised Progenitor Cells in Autologous Transplantation: In Vitro and In Vivo Aspects, J. Nutr. Sci. Vitaminol. (Tokyo). Spec No. 368-71 (1992).
M. Fukuda et al., Autotransplantation of Peripheral Blood Stem Cells Mobilized by Chemotherapy and Recombinant Human Granulocyte Colony-Stimulating Factor in Childhood Neuroblastoma and Non-Hodgkin's Lymphoma, British J. Haematology 80:327-331 (1992).
G. Morstyn et al., Treatment of Chemotherapy-Induced Neutropenia by Subcutaneously Administered Granulocyte Colony-Stimulating Factor With Optimization of Dose and Duration of Therapy, J. Clin. Onc., 7(10):1554-1562 (1989).
S. Neben et al., Mobilization of Hematopoietic Stem and Progenitor Cell Subpopulations from the Marrow to the Blood of Mice Following Cyclophosphamide and/or Granulocyte Colony-Stimulating Factor, Blood, 81(7):1960-1967 (1993).
R. Pettengell et al., Transplantation Potential of Hematopoietic Cells Released Into the Circulation During Routine Chemotherapy for Non-Hodgkin's Lymphoma, Blood, 82(7):2239-2248 (1993).
W.P. Sheridan et al., Effect of Peripheral-Blood Progenitor Cells Mobilised by Filgrastim (G-CSF) on Platelet Recovery After High-Dose Chemotherapy, The Lancet 339:640-644 (1992).
W.P. Sheridan, Transplantation of Mobilized Peripheral Blood Stem Cells: Role of Filgrastim, J. Hematotherapy 3:349-352 (1994).
Tsunemichi Shirota et al., Cyclophosphamide-induced Alterations of Bone Marrow Endothelium: Implications in Homing of Marrow Cells After Transplantation, Exp. Hematol. 19:369-373 (1991).
M.E.H.M. Van Hoef et al., Dose-Escalating Induction Chemotherapy Supported by Lenograstim Preceding High-Dose Consolidation Chemotherapy for Advanced Breast Cancer: Selection of the Most Acceptable Regimen to Induce Maximal Tumor Response and Investigation of the Optimal Time to Collect Peripheral Blood Progenitor Cells for Haematological Rescue After High-Dose Consolidation Chemotherapy, Ann. Oncol. 5:217-224 (1994).
Defendants' Invalidity Contentions, Case No. 3:16-cv-02581-RS, United States District Court Northern District of California San Francisco Division, pp. 1-119.
E. Breen et al. On the Mechanism of Mitochondrial Uncoupling Protein 1 Function, J. Biol. Chem., 281 (4):2114-2119 (2006).
M. Jaburek & K. D. Garlid. Reconstitution of Recombinant Uncoupling Proteins, J. Biol. Chem., 278 (28):25825-25831 (2003).
D. Johnson et al. Refolding, Purification, and Characterization of Human Erythropoietin Binding Protein Produced in *Escherichia coli*. Protein Expression and Purification 7:104-113 (1996).
K.Y. Kang et al. Purification and Characterization of a Recombinant Anti-Angiogenic Kringle Fragment Expressed in *Escherichia coli*: Purification and Characterization of a Tri-Kringle Fragment from Human Apolipoprotein (a), Protein Expression and Purification, 45:216-225 (2006).
Novagen, Inc. Protein Refolding Kit ("Novagen"), pp. 1-9, 1997-1998.
X.D. Wang et al. Perturbation of the antigen-binding site and staphylococcal Protein A-binding site of IgG before significant changes in global conformation during denaturation: an equilibrium study, Biochem. J. 325:707-710 (1997).
M. Yamasaki et al. Purification and Characterization of Recombinant Human Granulocyte Colony-Stimulating Factor (rhG-CSF) Derivatives: KW-2228 and Other Derivatives, Biosci. Biotechnol. Biochem. 62(8):1528-1534 (1998).
GE Healthcare Life Sciences "STREAMLINE SP, 300 ml" (http://www.gelifesciences.com/webapp/wcs/stores/servlet/catalog/en/

(56) References Cited

OTHER PUBLICATIONS

GELifeSciences/prod . . . ; date retrieved Dec. 9, 2015, SDZ(56)0259126, pp. 1); current version of webpage: http://www.gelifesciences.com/webapp/wcs/stores/servlet/productById/en/GELifeSciences-us/17099301(date retrieved Jul. 17, 2017).
Tosoh Bioscience GmbH, Toyopearl DEAE-650, http://www.separations.eu.tosohbioscience.com/ProductsPrinterFriendlyTemplate.aspx?N . . . ; date retrieved Dec. 9, 2015, pp. 1-2, SDZ(56)0259127; current version of webpage: http://www.separations.eu.tosohbioscience.com/solutions/process-media-products/by-mode/ion-exchange/anion-exchange/toyopearl-deae-650.
United States Patent and Trademark Office Before the Patent Trial and Appeal Board. (Feb. 17, 2017). Decision Granting Institution of Inter Partes Review 37 C.F.R. § 42.108: *Apotex Inc. and Apotex Corp.* Petitioner v. *Amgen Inc. and Amgen Manufacturing Limited*, Patent Owner (Case IPR2016-01542, U.S. Pat. No. 8,952,138 B2), pp. 1-35.
Unites States District Court for the Southern District of Florida. (Dec. 11, 2015). Document 77: *Amgen Inc. and Amgen Manufacturing Limited*, Plaintiffs, v. *Apotex Inc. and Apotex Corp.*, Defendants (Case No. 15-cv-61631-JIC/BSS), pp. 1-23.
Unites States District Court for the Southern District of Florida. (Dec. 11, 2015). Document 77-4: Exhibit 4, *Amgen Inc. and Amgen Manufacturing Limited*, Plaintiffs, v. *Apotex Inc. and Apotex Corp.*, Defendants (Case No. 15-cv-61631-JIC/BSS), pp. 1-16.
Unites States District Court for the Southern District of Florida. (Jan. 8, 2016). Document 83-1: Exhibit 1, *Amgen Inc. and Amgen Manufacturing Limited*, Plaintiffs, v. *Apotex Inc. and Apotex Corp.*, Defendants (Case No. 15-cv-61631-JIC/BSS), pp. 1-19.
Document 35: Answer and Affirmative Defenses to Complaint, Counterclaim against All Plaintiffs by Apotex Corp., Apotex Inc. (Brier, Simeon) (Entered: Oct. 5, 2015), pp. 1-41.
Document 42: Plaintiff's Motion for Preliminary Injunction and Incorporated Memorandum of Law by Amgen Inc., Amgen Manufacturing Limited, pp. 1-25. Attachments: # 1 Affidavit Declaration of Robert Azelby, pp. 1-4. # 2 Affidavit Declaration of Nicholas Groombridge, pp. 1-4. # 3 Exhibit A—Apr. 17, 2015 Letter to Groombridge-Pegfilgrastim, pp. 1-2. # 4 Exhibit B—May 8, 2015 Ltr. Groombridge to Coblentz re pegfilgrastim (1)(8)(A) notice, pp. 1-3. # 5 Exhibit C—Jul. 29, 2015 N Groombridge letter to B Coblentz, pp. 1-3. # 6 Exhibit D—Aug. 24, 2015 Letter to Groombridge, pp. 1-2. # 7 Exhibit E—May 5, 2015 Order Granting Motion for an Injunction Pending Appeal, pp. 1-3. # 8 Exhibit F—Joint Stip Re Amgens Motion for Preliminary Injunction Oct. 1, 2015, pp. 1-5. # 9 Exhibit G—FDA Website Printout, pp. 1-3. # 10 Exhibit H—Jorge Mestre-Ferrandiz, et al., The R&D Cost of a New Medicine (2012), pp. 1-101. # 11 Exhibit I—Oct. 16, 2015 Order Denying Petition for En Banc Rehearing, pp. 1-3. # 12 Text of Proposed Order Proposed Order)(O'Sullivan, John) (Entered: Oct. 16, 2015), pp. 1-2.
Document 47: Apotex's Corrected Answer, Affirmative Defenses & Counterclaims to Amgen's Complaint, Oct. 23, 2015, pp. 1-42.
Document 64: Defendants Apotex's Answer, Affirmative Defenses and Counterclaims to Plaintiffs' Complaint, Dec. 1, 2015, pp. 1-45.
Document 76: Apotex's Opening Claim Construction Brief, Dec. 11, 2015, pp. 1-26.
Document 77: Amgen's Opening Claims Construction Brief, Dec. 11, 2015, pp. 1-23; Document 77-1 to Exhibit 1, U.S. Pat. No. 8,952,138, document entered on Dec. 11, 2015, pp. 1-19; Document 77-2 to Exhibit 2, U.S. Pat. No. 6,162,427, document entered Dec. 11, 2015, pp. 1-7. Document 77-3 to Exhibit 3, U.S. Pat. No. 5,824,784, document entered Dec. 11, 2015, pp. 1-31. Document 77-4 to Exhibit 4, Declaration of Richard C. Willson, Ph. D. Regarding Claim Constructions of Shultz et al., document entered Dec. 11, 2015, pp. 1-16, Document 77-5 to Exhibit A, Richard Willson CV, document entered Dec. 11, 2015, pp. 1-21; Document 77-6 to Exhibit B, Effective renaturation of denatured and reduced immunoglobulin G in vitro without assistance of chaperone, document entered on Dec. 11, 2015, pp. 1-7. Document 77-7 to Exhibit C, Effective renaturation of reduced lysosome by gentle removal of urea, document entered on Dec. 11, 2015, pp. 1-6. Document 77-8 to Exhibit D, Perspectives in Biochemistry, *Biochemistry*, document entered on Dec. 11, 2015, pp. 1-10. Document 77-9 to Exhibit E, Structural Stability of Covalently Linked GroES Heptamer: Advantages in the Formulation of Oligomeric Structure, *Science Direct*, document entered on Dec. 11, 2015, pp. 1-16.
Document 82: Brief in response to Plaintiffs' Opening Claim Construction Brief by Apotex Corp., Apotex Inc. re 77 Trial Brief, documents entered on Jan. 8, 2016, pp. 1-25. Attachments: # 1 Declaration of W. Blake Coblentz in Support of Defendants Responsive Claim Construction Brief, pp. 1-2. # 2 Exhibit A—Declaration of Anne S. Robinson, Ph.D., pp. 1-17. # 3 Exhibit B—R. Rudolph and H. Lilie, In vitro folding of inclusion body proteins). Entered: Jan. 8, 2016, pp. 1-9.
Document 83: Responsive Claim Construction Brief by Amgen Inc., Amgen Manufacturing Limited. Documents entered on Jan. 8, 2016. pp. 1-25. Attachments: # 1 Affidavit Exh. 1—Rebuttal Declaration of Richard C. Willson, pp. 1-19. # 2 Exhibit A—Feb. 23, 2012 Office Action Response, pp. 1-6. # 3 Exhibit B—'370 Patent, pp. 1-167. # 4 Exhibit C—Jan. 29, 2014 Office Action, pp. 1-8. # 5 Exhibit D—Apr. 28, 2014 Office Action Response, # 6 Affidavit Exh. 2—Rebuttal Declaration of Louis M. Pelus, pp. 1-22. # 7 Exhibit A—Pelus CV, pp. 1-49. # 8 Exhibit B—Richman, pp. 1-11. # 9 Exhibit C—Shirota, pp. 1-8. # 10 Exhibit D—Neben, pp. 1-10.
Document 89: Apotex's Reply to Plaintiffs' Responsive Claim Construction Brief. Notice by Apotex Corp., Apotex Inc. re 83 Trial Brief,, Defendants Apotex Inc. and Apotex Corp.'s Reply to Plantiffs' Responsive Claim Construction Brief . Documents entered on Jan. 27, 2016, pp. 1-16. Attachments: # 1 Declaration of W. Blake Coblentz in Support of Defendants' Reply to Plaintiffs' Responsive Claim Construction Brief, pp. 1-2 # 2 Exhibit A—Excerpts of deposition transcript of Richard C. Willson, III, Ph.D., pp. 1-47 # 3 Exhibit B—Excerpts of deposition transcript of Anne Robinson, Ph.D., pp. 1-5 # 4 Exhibit C—Excerpts of deposition transcript of Louis M. Pelus, Ph.D. pp. 1-16.
Document 90: Amgen's Reply Claim Construction Brief. Document entered on Jan. 27, 2016, pp. 1-15. Attachments: Exhibit 1; Videotaped Deposition of Richard C. Willson, Ph. D. Jan. 18, 2016; pp. 1-109 Exhibit 2: Videotaped Deposition of Louis M. Pelus, Ph.D. Jan. 19, 2016; pp. 1-33. Exhibit 3: Transcript of the Testimony of Videotaped Deposition of Anne Robinson, Ph. D., Jan. 20, 2016; pp. 1-60. Exhibit 4: Videotaped Deposition of David T. Scadden, M.D. Jan. 22, 2016; pp. 1-43.
Document 184: Brief Plaintiff's Supplemental Claim Construction Brief Regarding the Meaning of "Protein" in Claim 1 of the '138 Patent by Amgen Inc., Amgen Manufacturing Limited. Documents Entered: Jun. 22, 2016), pp. 1-15. Attachments: # 1 Exhibit Ex. 1—U.S. Pat. No. 8,952,138, pp. 1-19. # 2 Exhibit Ex. 5—Jan. 18, 2016 Willson Dep. Tr. (Excerpt), pp. 1-12. # 3 Exhibit Ex. 6—Jun. 22, 2012 Response to Office Action from File History of U.S. Pat. No. 8,952,138)(O'Sullivan, John), pp. 1-6.
Document 186: Trial Brief Apotex's Supplemental Claim Construction Brief in Support of Their Construction for the Term 'protein' as Used in Claim 1 of U.S. Pat. No. 8,952,138 by Apotex Corp., Apotex Inc.pp. 1-18 (Attachments: # 1 Exhibit 1 U.S. Pat. No. 8,952,138; pp. 1-19; # 2 Exhibit 6—Response to Office Action dated Jun. 22, 2012)(Brier, Simeon) (Entered: Jun. 22, 2016); pp. 1-6.
Document 244: Motion for Judgment on Partial Findings Pursuant to Fed. R. Civ. P. 52(c) by Apotex Corp., Apotex Inc. pp, 1-12, Entered: Jul. 18, 2016: Attachments # 1 Exhibit A—Pages from Trial Transcript Day 1 (Jul. 11, 2016) (Willson), pp. 1-6 # 2 Exhibit B—Pages from Trial Transcript Day 2 (Jul. 12, 2016) (Willson), pp. 1-9 # 3 Exhibit C—Pages from Trial Transcript Day 3 (Jul. 13, 2016) (Dowd), pp. 1-13 # 4 Text of Proposed Order, pp. 1.
Document 247: Transcript of Bench Trial held on Jul. 11, 2016 before Judge James I. Cohn, 1-245 pages, Court Reporter: Karl Shires, 954-769-5496 / Karl_Shires@flsd.uscourts.gov. Transcript may be viewed at the court public terminal or purchased by contacting the Court Reporter/Transcriber before the deadline for Release of Transcript Restriction. After that date it may be obtained through PACER. Redaction Request due Aug. 11, 2016. Redacted Transcript Deadline set for Aug. 22, 2016. Release of Transcript Restriction set for Oct. 20, 2016. (Shires, Karl) (Entered: Jul. 18, 2016).

(56) References Cited

OTHER PUBLICATIONS

Document 248: Transcript of Bench Trial held on Jul. 12, 2016 before Judge James I. Cohn, 1-171 pages, Court Reporter: Karl Shires, 954-769-5496 / Karl_Shires@flsd.uscourts.gov. Transcript may be viewed at the court public terminal or purchased by contacting the Court Reporter/Transcriber before the deadline for Release of Transcript Restriction. After that date it may be obtained through PACER. Redaction Request due Aug. 11, 2016. Redacted Transcript Deadline set for Aug. 22, 2016. Release of Transcript Restriction set for Oct. 20, 2016. (Shires, Karl) (Entered: Jul. 18, 2016).

Document 249: Transcript of Bench Trial held on Jul. 13, 2016 before Judge James I. Cohn, 1-61 pages, Court Reporter: Karl Shires, 954-769-5496 / Karl_Shires@flsd.uscourts.gov. Transcript may be viewed at the court public terminal or purchased by contacting the Court Reporter/Transcriber before the deadline for Release of Transcript Restriction. After that date it may be obtained through PACER. Redaction Request due Aug. 11, 2016. Redacted Transcript Deadline set for Aug. 22, 2016. Release of Transcript Restriction set for Oct. 20, 2016. (Shires, Karl) (Entered: Jul. 18, 2016).

Document 250: Transcript of Bench Trial held on Jul. 14, 2016 before Judge James I. Cohn, 1-242 pages, Court Reporter: Karl Shires, 954-769-5496 / Karl_Shires@flsd.uscourts.gov. Transcript may be viewed at the court public terminal or purchased by contacting the Court Reporter/Transcriber before the deadline for Release of Transcript Restriction. After that date it may be obtained through PACER. Redaction Request due Aug. 11, 2016. Redacted Transcript Deadline set for Aug. 22, 2016. Release of Transcript Restriction set for Oct. 20, 2016. (Shires, Karl) (Entered: Jul. 18, 2016).

Document 254: Response in Opposition re 244 Motion for Judgment on Partial Findings Pursuant to Fed. R. Civ. P. 52(c) filed by Amgen Inc., Amgen Manufacturing Limited. Replies due by Aug. 15, 2016; pp. 1-20.

Document 259: Mandate of US Federal Circuit (certified copy) Affirm Judgment/ Order of the district court with courts opinion re 72 Notice of Appeal, filed by Apotex Corp., Apotex Inc. ; Date Issued: Aug. 11, 2016 ; US Federal Circuit Case No. 16-1308 (amb) (Entered: Aug. 11, 2016); pp. 1-26.

Document 260: Reply to Response to Motion re 244 Motion for Judgment on Partial Findings Pursuant to Fed. R. Civ. P. 52(c) filed by Apotex Corp., Apotex Inc. pp. 1-11; Attachments: # 1 Exhibit 1—Trial Transcript Day 2 (Jul. 12, 2016) (Willson), pp. 1-7. # 2 Exhibit 2—Trial Transcript Day 3 (Jul. 13, 2016) (Dowd), pp. 1-4. # 3 Exhibit 3—Trial Transcript Day 4 (Jul. 14, 2016) (Robinson), pp. 1-4. # 4 Exhibit 4—Trial Transcript Day 5 (Jul. 18, 2016), pp. 1-3.

Document 268: Final Judgment Signed by Judge James I. Cohn on Sep. 6, 2016. (tpl) Notice: If there are sealed documents in this case, they may be unsealed after 1 year or as directed by Court Order, unless they have been designated to be permanently sealed. See Local Rule 5.4 and Administrative Order 2014-69. (Entered: Sep. 6, 2016); pp. 1-5.

http://chemistry.umeche.maine.edu/CHY431/Ribo-fold.jpg.
UniProtKB—Q6EBC2 (IL31_HUMAN) UniProt (2016), pp. 1-8 http://www.uniprot.org/uniprot/Q6EBC2.
UniProtKB—Q6EAL8 (IL31_MOUSE) UniProt (2016), pp. 1-7.
IUPAC Gold Book—dalton (2016). Amgen Exhibit 2014 : *Apotex Inc et al*. V. *Amgen Inc. et al*., (IPR2016-01542), pp. 1.
Protein Structure Graphic http://pubs.rsc.org/services/images/RSCpubs.ePlatform.Service.FreeContent.ImageService.svc/ImageService/Articleimage/2014/TB/c4tb00168k/c4tb00168k-f2_hi-res.gif.
Protein Data Bank, Hen Egg White Lysozyme, http://www.rcsb.org/pdb/explore/explore.do?structureId=193L; http://www.rcsb.org/pdb/explore/remediatedSequence.do?structureId=193L.
DeBernadez Clark, Eliana, *Refolding of recombinant proteins*, Current Opinion in Biotechnology, vol. 9, pp. 157-163 (1998).

Kamau, Samuel M. et al. (2010). Alpha-Lactalbumin: Its Production Technologies and Bioactive Peptides. *Comprehensive Reviews in Food Science and Food Safety*, pp. 197-212, vol. 9.
Lehninger, Albert L. (1982). Chapter 17: Electron Transport, Oxidative Phosphorylation, and Regulation of ATP production. *Principles of Biochemistry*. New York, New York: Worth Publishers, Inc., pp. 1-46.
Lu et al. (May 5, 1992). Folding and Oxidation of Recombinant Human Granulocyte Colony Stimulating Factor Produced in *Escherichia coli*: Characterization of the disulfide-reduced intermediates and cysteine→Serine Analogs. *The Journal of Biological Chemistry*, pp. 8770-8777.
Phillips, David C. (1966). The Three-dimensional Structure of an Enzyme Molecule. Scientific American, pp. 78-90.
Schrodel and De Marco (May 31, 2015). Characterization of the aggregates formed during recombinant protein expression in bacteria. *BMC Biochemistry*. DOI: 10.1186/1471-2091-6-10, pp. 1-11.
Slanger, Charles J. et al. (1999). Use of Mass Spectrometry to Rapidly Characterize the Heterogeneity of Bovine α-Lactalbumin. *Department of Product Technology, BIZO Food Research*. vol 47, pp. 4549-4556.
Yamaguchi, Satoshi, et al. (2013). Protein refolding using chemical refolding additives. *Biotechnology Journal*, v (8), pp. 17-31.
United States Patent and Trademark Office Before the Patent Trial and Appeals Board. (Nov. 23, 2016). Patent Owners' Preliminary Response: *Apotex Inc. and Apotex Corp*. Petitioners v. *Amgen Inc. and Amgen Manufacturing Limited*, Patent Owners (Case IPR2016-01542, U.S. Pat. No. 8,952,138), pp. i-v, pp. 1-51.
United States Patent and Trademark Office Before the Patent Trial and Appeals Board. (Aug. 29, 2016). Patent Owner's Mandatory Notices: *Apotex Inc. and Apotex Corp*. Petitioners v. *Amgen Inc. and Amgen Manufacturing Limited*, Patent Owners (Case IPR2016-01542, U.S. Pat. No. 8,952,138), pp. 1-3.
United States Patent and Trademark Office Before the Patent Trial and Appeals Board. (Aug. 25, 2016). Notice of Filing Date Accorded to Petition and Time for Filing Patent owner Preliminary Response: *Apotex Inc. and Apotex Corp*. Petitioner v. *Amgen Inc. and Amgen Manufacturing Limited*, Patent Owner (Case IPR2016-01542, U.S. Pat. No. 8,952,138), pp. 1-5.
United States Patent and Trademark Office Before the Patent Trial and Appeals Board. (Aug. 25, 2016). Petition for Inter Partes Review of U.S. Pat. No. 8,952,138 Under 35 U.S.C. §§ 311-319 and 37 C.F.R. §§ 42.1-.80, 42.100-.123: *Apotex Inc. and Apotex Corp*. Petitioners v. *Amgen Inc. and Amgen Manufacturing Limited*, Patent Owner (Inter Partes Review No. IPR2016-01542), pp. i-viii, pp. 1-69.
United States Patent and Trademark Office Before the Patent Trial and Appeals Board. (Aug. 29, 2016). Updated Mandatory Notices for Patent Owners: *Apotex Inc. and Apotex Corp*. Petitioners v. *Amgen Inc. and Amgen Manufacturing Limited*, Patent Owners (Case IPR2016-01542, U.S. Pat. No. 8,952,138), pp. 1-4.
United States Patent and Trademark Office Before the Patent Trial and Appeal Board. (Nov. 23, 2016). Declaration, pp. 1-81, Curriculum Vitae of Richard C. Willson, PhD.pp. 1-7: *Apotex Inc. and Apotex Corp*. v. *Amgen Inc. and Amgen Manufacturing Limited* (Inter Partes Review No. IPR2016-01542, U.S. Pat. No. 8,952,138).
United States Patent and Trademark Office Before the Patent Trial and Appeal Board. (Aug. 5, 2016). Declaration pp. 1-74, Curriculum Vitae of Anne S. Robinson, PhD. pp. 1-7, Appendix A, pp. 1-4: *Apotex Inc. and Apotex Corp*. v. *Amgen Inc. and Amgen Manufacturing Limited* (Inter Partes Review No. IPR2016-01542).
United States Patent and Trademark Office. Notice of Allowance and Fees Due, U.S. Appl. No. 12/820,087, pp. 1-3.
United States Patent and Trademark Office. (Jan. 9, 2012). Information Disclosure Statement by Applicant, pp. 1-2.
Unites States District Court Southern District of Florida. (Apr. 7, 2016). Claim Construction Order, Document 119: *Amgen Inc. and Amgen Manufacturing Limited*, Plaintiffs, v. *Apotex Inc. and Apotex Corp*., Defendants (Case No. 15-61631-CIV-Cohn/Seltzer), pp. 1-12.
Unites States District Court Southern District of Florida. (Sep. 6, 2016). Findings of Fact and Conclusions of Law, Document 267: *Amgen Inc. and Amgen Manufacturing Limited*, Plaintiffs, v. *Apotex*

(56) References Cited

OTHER PUBLICATIONS

*Inc. and Apotex Corp.*, Defendants (Case No. 15-61631-CIV-COHN/SELTZER, Consolidated With 15-62081-CIV-COHN/SELTZER), pp. 1-30.
Unites States District Court for the Southern District of Florida. (Jul. 18, 2016). Partial Findings Regarding Apotexs Assertion of Invalidity of the 138 Patent. Signed by Judge James I. Cohn. Document 245: *Amgen Inc. and Amgen Manufacturing Limited*, Plaintiffs, v. *Apotex Inc. and Apotex Corp.*, Defendants (Case No. 15-cv-61631-JIC), pp. 1-5.
Gottschalk, U. "Filtration and Purification in the Biopharmaceutical Industry," ebook CRC Press 2007, eds. Maik W. Jornitz and Theodore H. Meltzer, $2^{nd}$ ed, pp. 459-495.
US District Court, Southern District of Florida; Case No. 15-61631-CIV-COHN (consolidated with 15-62081-CIV-COHN) *Amgen Inc. and Amgen Manufacturing Limited* v. *Apotex Inc. and Apotex Corp*; Defendants Apotex Inc. and Apotex Corp.; Invalidity Contentions; Dec. 1, 2015.
US District Court, Southern District of Florida; Case No. 15-cv-61631-JIC/BSS; *Amgen Inc. and Amgen Manufacturing Limited* v. *Apotex Inc. and Apotex Corp*; Defendants Apotex Inc. and Apotex Corp.; "Pegfil—Invalidity Contentions" Oct. 19, 2015.
Appendix A: Prior Art Chart for U.S. Pat. No. 8,952,138; Pegfil Invalidity Claim Chart 2015.
Hevehan and Clark, "Oxidative Renaturation of Lysozyme at High Concentrations," Biotechnology and Bioengineering, 1996, 54(3): 221-230.
Hakim and Benhar, "Inclonals," mAbs, published online May 1, 2009, 1:3, 281-287.
Whitford, "Proteins: Structure and Function," Sep. 1, 2005.
Johnson, "Human insulin from recombinant DNA technology". Science (1983) 219 (4585): 632-637.
Vallejo et al. "Strategies for the recovery of active proteins through refolding of bacterial inclusion body proteins," Microbial Cell Factories (2004) 3, 1-12.
Neubauer et al. "Protein inclusion bodies in recombinant bacteria. Inclusions in Prokaryotes." Microbiology Monographs Edited by: Shively JM. Springer; (2006) 237-292.
https://www.profacgen.com/inclusion-body-purification-protein-refolding.htm.
Georgiou and Valax, "Isolating Inclusion Bodies from Bacteria", Chapter 3 in Methods in Enzymology, vol. 309, p. 48-58 (1999) Academic Press.
Palmer and Wingfield "Preparation and Extraction of Insoluble (Inclusion-Body) Proteins from *Escherichia coli*" Curr Protoc Protein Sci. Nov. 2004; Chapter: Unit—6.3. doi:10.1002/0471140864. ps0603s38.
Shortle et al., "Clustering of Low-Energy Conformations Near the Native Structures of Small Proteins," Proc Natl Acad Sci (1998) 95, 11158-62.
Panda, "Bioprocessing of Therapeutic Proteins from the Inclusion Bodies of *Escherichia coli*" Adv Biochem Engin/Biotechnol (2003) 85: 43-93.
Vincentelli, "High-throughput automated refolding screening of inclusion bodies," Protein Science (2004) 13:2782-2792.
Willis et al., "Investigation of protein refolding using a fractional factorial screen: A study of reagent effects and interactions." Protein Science (2005) 14(7), 1818-1826.
Jungbauer and Kaar "Current status of technical protein refolding," Journal of Biotechnology 128 (2007) 587-596.
Ferrer-Miralles et al. "Microbial factories for recombinant pharmaceuticals" Microbial Cell Factories (2009) 8:17.
Graumann and Premsaller, "Manufacturing of recombinant therapeutic proteins in microbial systems," Biotech J. (2006) 1:164-186.
Xie and Wetlaufer, "Control of aggregation in protein refolding: The temperature-leap tactic," Protein Science (1996) 5:517-523.
Puri, "Refolding of recombinant porcine growth hormone in a reducing environment limits in vitro aggregate formation," FEBS (1991) vol. 292, No. 1.2, 187-190.

Ejima, "High yield refolding and purification process for recombinant human interleukin-6 expressed in *Escherichia coli*," Biotechnology and Bioengineering (1999) vol. 62, No. 3, 301-310.
Patra et al., "Optimization of inclusion body solubilization and renaturation of recombinant human growth hormone from *Escherichia coli*," Protein Expression and Purification (2000) 18, 182-192.
Mannall et al., "Factors Affecting Protein Refolding Yields in a Fed-Batch and Batch-Refolding System," Biotechnology and Bioengineering, (2007) vol. 97, No. 6, 1523-1534.
Misawa and Kumagai "Refolding of Therapeutic Proteins Produced in *Escherichia coli* as Inclusion Bodies" Biopoly (1999) 51: 297-307.
Park et al., "A Divalent Recombinant Immunotoxin Formed by a Disulfide Bond between the Extension Peptide Chains," Mol. Cells (2001) vol. 12, No. 3, 398-402.
EnbrelTM (etanercept) label, Nov. 1998.
Bolado, "Amgen Opens Trial in Fight Over Neulasta Generic," Law360, Jul. 11, 2016 (http://www.law360.com/articles/814748/amgen-opens-trial-in-fight-over-neulasta-generic).
Maurer et al., "Folding and aggregation of a multi-domain engineered immunotoxin," Biochemical Engineering Journal (2013) 81:8-14.
Sereikaite et al., "Production of recombinant mink growth hormone in *E. coli*," Appl Microbiol Biotechnol (2007) 74:316-323.
Shimamoto et al., "Peptibodies: A flexible alternative format to antibodies," mAbs (Sep./Oct. 2012) 4:5, 586-591.
http://pubs.rsc.org/services/images/RSCpubs.ePlatform.Service.FreeContent.ImageService.svc/ImageService/Articleimage/2014/TB/c4tb00168k/c4tb00168k-f2_hi-res.gif.
Bowden et al., "Structure and morphology of protein inclusion bodies in *Escherichia coli*" Bio/Tech (1991) 9:725-730.
Weiss et al. "Principles, Approaches, and Challenges for Predicting Protein Aggregation Rates and Shelf Life" J Pharm Sci. Apr. 2009; 98(4):1246-77.
Ventura and Villaverde "Protein quality in bacterial inclusion bodies" TRENDS in Biotechnology vol. 24 No. 4 Apr. 2006.
Cowley & Mackin, "Expression, purification and characterization of recombinant human proinsulin," FEBS Lett 402: 124-130 (1997).
Rudolph & Lilie, "In vitro folding of inclusion body proteins," Faseb J. 10: 49-56 (1996).
Creighton, T.E., "Renaturation of the reduced bovine pancreatic trypsin inhibitor," J. Mol. Biol. 87: 563-577, (1974).
Stöckel, J. et al., "Pathway of detergent-mediated and peptide ligand-mediated refolding of heterodimeric class II major histocompatibility complex (MHC) molecules," Eur J. Biochem 248: 684-691 (1997).
St. John et al., "High pressure refolding of recombinant human growth hormone from insoluble aggregates. Structural transformations, kinetic barriers, and energetics," J. Biol. Chem. 276(50): 46856-63 (2001).
Lilie, Schwarz & Rudolph, "Advances in refolding of proteins produced in *E. coli*," Current Opinion in Biotechnology 9(5): 497-501 (1998).
Tran-Moseman, Schauer & Clark, "Renaturation of *Escherichia coli*-derived recombinant human macrophage colony stimulating factor," Protein Expression and Purification 16(1): 181-189 (1999.
Darby, N.J. et al., "Refolding of bovine pancreatic trypsin inhibitor via non-native disulphide intermediates," J. Mol. Biol. 249(2): 463-477, (1995).
Snyder et al., "Characterization of DC-SIGN/R Interaction with Human Immunodeficiency Virus Type 1 gp 120 and ICAM Molecules favors the receptor's role as an antigen-capturing rather than an adhesion receptor," J. Virology 79(8): 4589-4598, Apr. 2005.
Javaherian, K. et al., "Laminin Modulates Morphogenic Properties of the Collagen XVIII Endostatin Domain," J. Biol. Chem. 277(47):45211-45218, Nov. 22, 2002.
GE Healthcare Instructions 71-7089-00AE: Affinity media, Protein A Sepharose CL-4B, p. 1-8, Mar. 2006. (Cited in JP Office action as D5 http://eclub.biomart.cn/sites/eclub.biomart.cn/themes/aktaclub/Files/71708900AE_UM_Protein_A_Sepharose_CL-4B.pdf, Mar. 2006).
GE Healthcare Instructions 71-5002-60 AE: Ion exchange chromatography; Q Sepharose XL, XL virus licensed, SP Sepharose XL, pp. 1-16, Feb. 2006 (cited in JP Office action as D6https://www.

(56) References Cited

OTHER PUBLICATIONS gelifesciences.com/gehcls_images/GELS/Related%20Content/Files/1314723116657/litdoc71500260AE_20110830185637.pdf, Feb. 2006).
Pavlinkova et al., Charge-Modified Single Chain Antibody Constructs of Monoclonal Antibody CC4: Generation, Characterization, Pharmokinetics and Biodistribution Analysis (Nuclear Med. Biol., vol. 26, pp. 27-34, 1999.
Ronnmark et al, "Construction and characterization of affibody-Fc chimeras produced in *Escherichia coli*" (Journal of Immunological Methods, 261:199-211, 2002).
Tengliden, "Development of Cleaning-in-Place Procedures for Protein A Chromatography Resins Using Design of Experiments and High Throughput Screening Technologies", Masters Thesis, Linkoping University, Feb. 2008).
Arvidsson, P. et al., "Direct chromatographic capture of enzyme from crude homogenate using immobilized metal affinity chromatography on a continuous supermacroporous adsorbent," Journal of Chromatography 986 (2): 275-290 (2003).
Ling et al., "Integration of mechanical cell disruption and fluidised bed recovery of G3PHD from unclarified disrupted 2 yeast: a comparative study of the performance of unshielded and polymer shielded dye-ligand chromatography systems," J. Biotech. 119(4): 436-448 (2005).
Fischer, B. et al., "Isolation renaturation and formation of disulfide bonds of eukaryotic proteins expressed in *Escherichia coli* as inclusion bodies," Biotech. and Bioengineering, 41 (1): 3-13 (1993).
Ford et al., "Affinity purification of novel bispecific antibodies recognising carcinoembryonic antigen and doxorubicin," J. Chromatogr. B, 754: 427-435 (2001).
Shukla et al., "Downstream processing of monoclonal antibodies—Application of platform approaches," Journal of Chromatography B, 848(1 ):28-39 (2007).
Wang et al., "Perturbation of the antigen-binding site and staphylococcal protein A-binding site of IgG before significant changes in global conformation during denaturation: an equilibrium study," Biochem. J. 325(Part 3):707-710 (1997).
Hasemann & Capra, "Immunoglobulins: Structure and Function," in William E. Paul, ed., Fundamental Immunology, Second Edition, 209, 210-218 (1989).
Ostrove, "Affinity Chromatography: General Methods," Guide to Protein Purification, Methods in Enzymology 182: 371-379 (1990).
Devereux et al., "A comprehensive set of sequence analysis programs for the VAX," Nucleosides, nucleotides & nucleic acids: Nucl. Acids Res. 12: 387-389 (1984).
Gribskov and Burgess, "Sigma factors from *E. coli*, B. subtilis, phage SP01, and phage T4 are homologous proteins," Nucl. Acids Res. 14: 6745 (1986).
Gulich, Susanne, et al., "Protein engineering of an IgG-binding domain allows milder elution conditions during affinity chromatography," J. Biol. 76, Issues 2-3, pp. 233-244 (2000).
Ostrove, "Affinity Chromatography: General Methods," Guide to Protein Purification, Methods in Enzymology 182: 357-371 (1990).
Stoscheck, C., "Quantitation of Protein," Guide to Protein Purification, Methods in Enzymology 182: 50-68 (1990).
Vola et al., "Recombinant proteins Land LG. Two new tools for purification of murine antibody fragments," Cell Biophys. 24-25: 27-36 (1994).
Aybay and Imir, "Development of a rapid, single-step procedure using protein G affinity chromatography to deplete fetal 12 calf serum of its IgG and to isolate murine IgG1 monoclonal antibodies from supernatants of hybridoma cells," Int'l. J. Immunol. Methods 233(1-2): 77-81 (2000).
Ejima, Daisuke, et al., Effective elution of antibodies by arginine and arginine derivatives in affinity col. chromatography, Analytical Biochem. 345250-257 (2005).
Arakawa, Tsutomu et al., "Elution of antibodies from a Protein-A column by acqueous arginine solutions," Protein Express & Purif., 36: 244-248 (2004).

Miller, Timothy et al., The rapid isolation of ribonuclease-free immunoglobulin G by protein A-sepharose affinity chromatography, J. Immun. Methods 24: 111-125 (1978).
Singh et al., "Solubilation and Refolding of Bacteria Inclusion Body Proteins," J. Bioscience and Bioengineering, vol. 99(4), pp. 3o3-310 (2005).
DeBernadez Clark, Eliana, "Protein Refolding for industrial processes," Current Opinion in Biotechnology, vol. 12, pp. 202-207 (2001).
De Berndez Clark, Eliana, et al. "Oxidative Renaturation of Hen Egg-White Lysozyme. Folding vs aggregation." Biotechnol. Prog. 14: 47-57 (1998).
Initial Invalidity Contentions for U.S. Pat. No. 9,643,997 filed in the United States District Court for the District of Delaware, in *Amgen Inc. and Amgen Manufactucturing, Limited v. Hospira, Inc. and Pfizer Inc.*, C.A. No. 18-cv-01064 CFC, Jan. 11, 2019, 44 pages.
Chaozhan Wang et al., Refolding Recombinant Human Granulocyte Colony Stimulating Factor Expressed by *E. coli*, 4 Bioprocess Int'l 48 (2006).
Chaozhan Wang et al., Renaturation with Simultaneous Purification of rhG-CSF from *Escherichia coli* by Ion Exchange Chromatography, 21 Biomedical Chromatography 1291 (2007).
Naoko Sakihama et al., Toyopearl HW-65C: Ammonium Sulfate as a New Column Chromatographic Adsorbent for Enzyme Purification, 93 J. Biochemistry 129 (1983).
Masayuki Shimao et al., Pyrroloquinoline Quinone as an Essential Growth Factor for a Polyvinyl Alcohol)-Degrading Symbiont, *Psudomonas* sp. VM15C, 48 Agric. &Biological Chemistry 2873 (1984).
Reiko Urade et al., Protein Degradation by the Phosphoinositide-specific Phospholipas C-α Family from Rat Liver Endoplasmic Reticulum, 267 J. Biological Chemistry 15152 (1992).
Thomas Zink et al., Secondary Structure of Human Granulocyte Colony-Stimulating Factor Derived from NMR Spectroscopy, 314 FEBS Letters 435 (1992).
Tosoh Bioscience, Toyopearl Instruction Manual (1996), 20 pages.
USPTO, Petition for Inter Partes Review of U.S. Pat. No. 9,856,287 BI, Dec. 20, 2019, pp. 1-79.
Bollag, D et al., Protein Methods, (John Wiley Sons, 2nd ed. 1996).
Creighton, T., Encyclopedia of Molecular Biology (John Wiley Sons, vols. 1-4, 1999).
Cutler, P., Protein Purification Protocols (Humana Press, 2nd ed., 2004) ("Cutler").
Declaration of Dr. Peter M. Tessier, Ph.D. in Support of Petition for Inter Partes Review of U.S. Pat. No. 9,643,997.
Deutscher, M. Methods in Enzymology: vol. 182 Guide to Protein Purification (Academic Press, 1999).
File History for U.S. Pat. No. 9,643,997.
GE Healthcare, Purifying Challenging Proteins: Principles and Methods (General Electric Company, 2007).
GE Healthcare, Recombinant Protein Purification Handbook: Principles and Methods (General Electric Company, 2000).
Ion Exchange Chromatography Chromatofocusing: Principles and Methods (Amersham Biosciences, ed. AA, 2004).
IPR2019-001183-997—Petition for Inter Partes Review, Jun. 8, 2019.
IPR2019-01183 Amgens Opening Claim Construction Brief, dated Jun. 1, 2018.
IPR2019-01183 Amgens Reply Claim Construction Brief, Dated Jul. 20, 2018.
Protein Purification—Handbook (Amersham Biosciences, ed. AC, 2001).
Stirling, P. et al., "Getting a grip on non-native proteins," European Molecular Biology Organization 4(6):565-570 (2003).
Wang, C. et al., "Solubilization and Refolding with Simultaneous Purification of Recombinant Human Stem Cell Factor," Appl Biochem Biotechnol (2008) 144:181-189 (2008) ("Wang").
Ge Healthcare 2007. Purifying Challenging Proteins: Principles and Methods. GE Healthcare Bio-Sciences AB, Uppsala, Sweden.
Pierce Biotechnology, Inc. 2003. Instructions for Pro-Matrix(TM) Protein Refolding Kit No. 89867.
European Patent Office, Notice of opposition to a European patent, Jun. 6, 2019.

(56) References Cited

OTHER PUBLICATIONS

European Patent Office, Enclosure in Notice of opposition to a European patent, Jun. 6, 2019: Final TPR and TPBS Calculations for D11 [WO1999042486A1] Example 4, Jun. 6, 2019.
European Patent Office, Annex to the Notice of Opposition Against EP 2445923B Amgen, Inc. Facts and Arguments in Accordance with Rule 76(2)(c)EPC, Jun. 6, 2019.
Mittl, P.R.E. and Grutter, M.G. (2001) Current Opinion in Chemical Biology, 5: 402-408.
W L Anderson and D B Wetlaufer, The folding pathway of reduced lysozyme, J. Biol. Chem. 1976, 251:3147-3153.
IPR2019-01183 No. 33 Termination Decision *Kabi* v *Amgen*, U.S. Pat. No. 9,643,997 entered Jun. 23, 2020.
IPR2019-001183 Patent Owner's Response, *Kabi* v *Amgen*, U.S. Pat. No. 9,643,997, May 15, 2020.
IPR2020-00314 No. 17 Termination due to Settlement before Trial *Kabi* v *Amgen*, U.S. Pat. No. 9,856,287 entered Jun. 19, 2020.
Deposition of Peter M. Tessier, PhD, Detroit, MI, Mar. 3, 2020.
Curriculum Vitae of Professor Peter M. Tessier, PhD, Detroit MI, Mar. 3, 2020.
Materials Reviewed by Professor Peter M. Tessier, PhD, Detroit MI, Mar. 3, 2020.
Chi et al "Physical Stability of Proteins in Aqueous Solution: Mechanism and Driving Forces in Nonnative Protein Aggregation", Pharmaceutical Research, vol. 20, No. Sep. 9, 2003, Springer, Switzerland.
Extended European Search Report for European application No. 19209054.6, 8 pages, dated Apr. 24, 2020.
IPRP2019-001183, Expert Declaration of Chenming (Mike) Zhang, U.S. Pat. No. 9,643,997, May 15, 2020.
IPRP2021-00326, Expert Declaration of George Georgiou, PhD, U.S. Pat. No. 9,856,287, Dec. 15, 2020.
IPRP2021-00326, Petition for Inter Partes Review of U.S. Pat. No. 9,856,287, *Lupin, LTD and Lupin Pharmaceuticals, Inc.* v. *Amgen Inc.*, Dec. 15, 2020.
USPTO, Patent and Trial Appeal Board, IPR2021-00326 Decision Denying Institution of Inter Partes Review, p. 3¬-13, Jul. 12, 2021, Alexandria, VA, USA.
Notice of Opposition issued for corresponding European Application EP 10 729 997.6, 25 pages, dated Dec. 3, 2021.
De Bernardez Clark et al "Inhibition of aggregation side reactions during in Vitro protein folding", Methods in Enzymology, 309, 217-236, 1999, Academic Press.
SIB Swiss Institute of Bioinformatics "Expasy MW calculation for SEQ ID No. 618" https://web.expasy.org/cgi-bin/compute_pi/pi_tool; retrieved Sep. 17, 2021.
SIB Swiss Institute of Bioinformatics "Expasy MW calculation for SEQ ID No. 646, 650, 654, and 658" https://web.expasy.org/cgi-bin/compute_pi/pi_tool; retrieved Sep. 19, 2021.
Fahrner et al "Industrial purification of pharmaceutical antibodies: development, operation, and validation of chromatography processes"; Biotechnology and Genetic Engineering Reviews, 18:1, 301-327, 2001, Taylor and Francis.
Fisher et al. "The high throughput purification of Fc-fusion proteins" Process Biochemistry 41, 2473-2476, 2006, Elsevier Science.
Datasheet for Mab Select Resin Development, GE Healthcare, Jun. 2007.
Stridsberg-Friden"Protein A Chromatography Resin Development", GE Healthcare, 2017.
Lute et al. "Robustness of virus removal by protein A chromatography is independent of media lifetime", Journal of Chromatography A, 1205, 17-25, 2008, Elsevier Science.
HiTrap Mab Select Sure product information sheet, GE Healthcare, Sep. 2007.
MEP HyperCel product information sheet, BioSepra, Jul. 2007.
IPRP2016-01542, Appeal from the United States Patent and Trademark Office, *Amgen* v *Katherine K. Vidal*, Apr. 14, 2022.
Summons to Attend Oral proceedings issued for corresponding European Application EP 10 729 997.6, 24 pages, dated Sep. 9, 2022.
Submission in Opposition Proceedings following Summons to Attend Oral proceedings for corresponding European Application EP 10 729 997.6, 14 pages, dated Feb. 10, 2023.
Letter Accompanying Subsequently Filed Items for corresponding European Application EP 10 729 997.6, 57 pages, dated Feb. 10, 2023.
Minutes of the Oral Proceedings before the Opposition Division for corresponding European Application EP 10 729 997.6, 501 pages, dated May 8, 2023.
Provision of the Minutes in Accordance with Rule 124(4) EPC for corresponding European Application EP 10 729 997.6, 14pages, dated May 8, 2023.
Minutes of the Oral Proceedings before the Opposition Division for corresponding European Application EP 10 729 997.6, 15 pages, dated May 8, 2023.
Interlocutory Decision in Opposition Proceedings for corresponding European Application EP 10 729 997.6, 49 pages, dated May 8, 2023.
Interlocutory Decision in Opposition Proceedings (Art. 101(3)(a) and 106(2) (EPC) for corresponding European Application EP 10 729 997.6, 16 pages, dated May 8, 2023.
Andersson, Maria et al., Assignment of Interchain Disulfide Bonds in Platelet-derived Growth Factor (PDGF) and Evidence for Agonist Activity of Monomeric PDGF, 267 J. Biological Chem. 11260 (1992).
Thatcher, David R., Recovery of Therapeutic Proteins from Inclusion Bodies: Problems and Process Strategies, 18 Biochem. Society Transactions 234 (1990).
GE Healthcare, Instructions 71-7100-00AC Ion Exchange, DEAE Sephacel, SDZ(56)0259118, pp. 1-8.
Seetharama Acharya, A. Taniuchi, Hiroshi, A Study of Renaturation of Reduced Hen Egg White Lysozyme, 251 J. Biological Chem. 6934 (1976).
Hill, Mark, Embryology Human Chronic Gonadtropin, UNSW Embryology, https://embryology.med.unsw.edu.au/embryology/index.php/Human_Chorionic_Gonadotropin.
Kliemannel, Marco et al., The Mature Part of proNGF Induces the Structure of its Propeptide, 556 FEBS Letters 207 (2004).
Pan, Siqi et al., Engineering Batch and Pulse Refolding with Transition of Aggregation Kinetics: An Investigation Using Green Fluorescent Protein (GFP), 131 Chemical Eng"g Sci. 91 (2015).
"How to Fold Graciously," Mossbaun Spectroscopy in Biological Systems Proceedings, Univ. of Illinois Bulletin, 67, No. 41, 22-24 (1969).
"Lenders Presentation" by Amneal Pharmaceuticals LLC and Impax Laboratories (Mar. 7, 2018).
Adellobio "Purpose-driven Products", Adello Pipeline, Mar. 1, 2018 http://adellobio.com/pipeline.
*Amgen Inc et al.* v. *Adello Biologics LLC*, Case No. 2:18-cv-03347 (D.N.J.), DE47 (Oct. 1, 2018 letter to U.S. Magistrate Judge Mark Falk).
*Amgen Inc et al.* v. *Adello Biologics LLC*, Case No. 2:18-cv-03347 (D.N.J.), DE1 (Amgens Complaint), Oct. 1, 2018.
*Amgen Inc et al.* v. *Adello Biologics LLC*, Case No. 2:18-cv-03347 (D.N.J.), DE50 (Amgens Amended Complaint), Oct. 1, 2018.
*Amgen Inc et al.* v. *Adello Biologics, LLC*, Case No. 2:18-cv-03347 (D.N.J.), DE54 (Defendant Adello Biologics, LLCs Answer, Defenses and Counterclaims to Plaintiffs First Amended Complaint), Oct. 1, 2018.
*Amgen Inc et al.* v. *Adello Biologics, LLC*, Case No. 2:18-cv-03347 (D.N.J.), DE57 (Amneal Pharmaceuticals, Inc. Proof of Service), Oct. 1, 2018.
*Amgen Inc et al.* v. *Adello Biologics, LLC*, Case No. 2:18-cv-03347 (D.N.J.), DE58 (Amneal Pharmaceuticals, LLC Proof of Service), Oct. 1, 2018.
*Amgen Inc et al.* v. *Adello Biologics, LLC*, Case No. 2:18-cv-03347 (D.N.J.), DE59 (Miller Appearance for Amneal Pharmaceuticals, LLC and Amneal Pharmaceuticals, Inc.), Oct. 1, 2018.
*Amgen Inc et al.* v. *Adello Biologics, LLC*, Case No. 2:18-cv-03347 (D.N.J.), DE60 (Gabay Appearance for Amneal Pharmaceuticals, LLC and Amneal Pharmaceuticals, Inc.), Oct. 1, 2018.

(56) References Cited

OTHER PUBLICATIONS

*Amgen Inc et al.* v. *Adello Biologics, LLC*, Case No. 2:18-cv-03347 (D.N.J.), DE70-1 (Brief in Support of Motion to Dismiss), Oct. 1, 2018.
*Amgen Inc.* v. *Apotex Inc.*, Appeal No. 17-1010 (Fed. Cir.), DE 423 (Joint Appendix vol. III of III), Oct. 1, 2018.
Amneal Pharmaceuticals LLC, M A Call Transcript (Oct. 17, 2017).
Amneal Pharmaceuticals, Inc., Form S-1 (May 7, 2018).
Anfinsen, "Principles that Govern the Folding of Protein Chains," Science, vol. 181, No. 4096, 223-230 (1973).
Business Wire "FDA Accepts Adellos Biosimilar License Application (BLA) for a proposed Filgrastim Biosimilar" Sep. 11, 2017, http://www.businesswire.com/news/home/20170911005971/en.
Chiti et al., "Conformational Stability of Muscle Acylphosphatase: The Role of Temperature, Denaturant Concentration, and pH," Biochemistry, 37:1447-55 (1998).
Daopin et al., "Crystal Structure of Transforming Growth Factor-02: An Unusual Fold for the Superfamily," Science, vol. 257, 369-373 (1992).
PGR2019-00001—Declaration of Catherine Nyarady in Support of Patent Owner's Preliminary Response to Petition for Post Grant Review of U.S. Pat. No. 9,856,287.
PGR2019-00001—Declaration of Saurabh Gupta in Support of Patent Owner's Preliminary Response to Petition for Post Grant Review of U.S. Pat. No. 9,856,287.
Dimasi et al."Innovation in the Pharmaceutical Industry: New Estimates of R D Costs" Journal of Health Economics, 47 (2016) pp. 20-33, Elsevier Science.
Email from counsel for Amgen to counsel for Petitioner Adello Biologics, LLC, dated Sep. 19, 2018, and attachments.
Email from counsel for Petitioners to the Board, dated Jan. 15, 2019.
Emails between counsel for Petitioners and counsel for Patent Owners, dated Jan. 2, Jan. 8, Jan. 10, and Jan. 11, 2019.
Excerpts from file history of U.S. Appl. No. 14/611,037, filed Jan. 30, 2015.
Excerpts from file history of U.S. Appl. No. 15/422,327, filed Feb. 1, 2017.
Food and Drug Administration"Biosimilar Biological Product Reauthorization Perfomance Goals and Procedures Fiscal Years 2018 Through 2022" https://www.fda.gov/downloads/forindustry/userfees/biosimilaruserfeeactbsufa/ucm521121.pdf.
Gaspar et al., "Cysteine 116 Participates in Intermolecular Bonding of the Human VEGF Homodimer," Archives of Biochemistry and Biophysics, 404, 126-135 (2002).
https://embryology.med.unsw.edu.au/embryology/index.php/Human_C horionic_Gonadotropin, Feb. 4, 2019.
Impax Laboratories, Inc., Schedule 14A (Feb. 12, 2018).
Jahn and Radford, "Folding Versus Aggregation: Polypeptide Conformations on Competing Pathways," Archives of Biochemistry and Biophysics, 469, 100-117 (2008).
Kliemannel et al., "The Mature Part of proNGF Induces the Structure of its Pro-Peptide," FEBS Letters, 566, 207-212 (2004).
Kuwajima, "The molten globule state of a-lactalbumin", FASEB (1996) 10:102-109.
Luis Felipe Vallejo Ursula Rinas, Optimized Procedure for Renaturation of Recombinant Human Bone Morphogenetic Protein-2 at High Protein Concentration, Biotechnology and Bioengineering, vol. 85 No. 6, 601-09 (Mar. 2004).
PGR2019-00001—Decision—Institution of Post Grant Review, Apr. 19, 2019.
PGR2019-00001—Patent Owners Preliminary Response, Jan. 23, 2019.
PGR2019-00001—Patent Owners Objections to Evidence, May 3, 2019.
PGR2019-00001—Patent Owners Opp. to Petitioners Mtn to Suspend, Feb. 4, 2019.
PGR2019-00001—Petitioners Motion to Amend Notices and Patent Owner Req discovery, Feb. 14, 2019.
PGR2019-00001 Table of categorized claims for U.S. Pat. No. 9,856,287, Feb. 14, 2019.
Righetti et al., "Folding/unfolding/refolding of proteins: present methodologies in comparison with capillary zone electrophoresis," Electrophoresis, 22, 2359-74 (2001).
Amersham Biosciences, Ion Exchange Chromatography Chromatofocusing: Principle and Methods, No. 11-0004-21, Amersham Biosciences Limited (GE Healthcare) (Ed. AA) (2004) ("GE Handbook") PT1.
Amersham Biosciences, Ion Exchange Chromatography Chromatofocusing: Principle and Methods, No. 11-0004-21, Amersham Biosciences Limited (GE Healthcare) (Ed. AA) (2004) ("GE Handbook") PT2.
Amersham Biosciences, Ion Exchange Chromatography: Principle and Methods, No. 18-1114-21, Amersham Biosciences (Ed. AA) (2003) PT 1.
Amersham Biosciences, Ion Exchange Chromatography: Principle and Methods, No. 18-1114-21, Amersham Biosciences (Ed. AA) (2003) Pt 2.
*Amgen* v. *Hospira Claim Construction* Transcript, C.A. No. 18-1064-CFC (D. Del. May 15, 2019).
Amgens Responses to Adellos Invalidity Contentions, C.A. No. 1:18-cv-03347-CCC-MF (D.N.J. Nov. 6, 2018).
Amgens Responses to Defendants Invalidity Contentions, C.A. No. 1:18-cv-03347-CCC-MF (D.N.J. Apr. 19, 2019).
Ann-Kristin Barnfield Frej et al., "Pilot Scale Recovery of Recombinant Annexin V from Unclarified *Escherichia coli* Homogenate Using Expanded Bed Adsorption," Biotechnology and Bioengineering, 44:922-929 (1994).
Apr. 1, 2016, Amgens Opening Claim Construction Brief, in *Amgen Inc et al.* v. *Sandoz Inc et al.*, 14-cv-04741-RS (N. D. Cal.).
Defendant Adello Biologics, LLCs Answer Defenses, and Counterclaims to Plaintiffs Second Amended Complaint, C. A. No. 1:18-cv-03347-CCC-MF (D.N.J. Feb. 21, 2019).
Defendant Adello Biologics, LLCs Preliminary Invalidity Contentions Pursuant to L. Pat. R. 3.3, C.A. No. 1:18-cv-03347-CCC-MF (D.N.J. Oct. 5, 2018).
Fred Regnier, "High Performance Ion-Exchange Chromatography," Methods in Enzymology, 104:170-189 (1984).
GE Healthcare, Affinity Chromatography: Principle and Methods, No. 18-1022-29, General Electric Company (2007).
George L. Mayers and Carel J. van Oss, "Affinity Chromatography," in Encyclopedia of Immunology. 2nd Edition. Academic Press, Table of Contents and pp. 47-49. (1998).
Hans Neurath et al., "The Denaturation of Proteins and its Apparent Reversal. II. Horse Serum Pseudoglobulin," J. Phys. Chem., 46:203-211 (1942).
Harvey Lodish et al. Molecular Cell Biology. 4th edition. New York: W. H. Freeman; 2000. Section 3.5, Purifying, Detecting, and Characterizing Proteins. Available from: https://www.ncbi.nlm.nih.gov/books/NBK21589/.
IPR2019-00797 *Kashiv Biosciences* v *Amgen*, Petition For Inter Partes Review, (997), Mar. 7, 2019.
IPR2019-00797 Appendix 4-B: Response to Adellos Invalidity Contentions Against the 997 Patent (Komath), Mar. 7, 2019.
IPR2019-00797 Declaration of Anne S. Robinson, Ph.D., Mar. 7, 2019.
IPR2019-00797 Declaration of Naz Wehrli, Mar. 7, 2019.
IPR2019-00797 Declaration of Sayem Osman, Mar. 7, 2019.
IPR2019-00797 Joint Claim Construction Chart, C.A. No. 18-1064-CFC (D. Del. Feb. 8, 2019).
IPR2019-00797, Patent Owners Preliminary Response (997), Jun. 14, 2019.
Jul. 13, 2016 Transcript of Claim Construction Hearing, held on Jul. 1, 2016, in *Amgen Inc et al.* v. *Sandoz Inc et al.*, 14-cv-04741-RS (N.D. Cal.).
Jul. 20, 2018 Amgens Reply Claim Construction Brief, in *Amgen Inc., et al.* v. *Mylan Inc et al.*, 2:17-cv-01235 (W.D. Pa.).
Jun. 1, 2018 Amgens Opening Claim Construction Brief, in *Amgen Inc., et al.* v. *Mylan Inc et al.*, 2:17-cv-01235 (W.D. Pa.).
Jun. 1, 2018 Declaration of Richard C. Willson in support of Amgens Opening Claim Construction Brief, in *Amgen Inc., et al.* v. *Mylan Inc et al.*, 2:17-cv-01235 (W.D. Pa.).

(56) References Cited

OTHER PUBLICATIONS

Lawrence Haff et al., "Use of Electrophoretic Titration Curves for Predicting Optimal Chromatographic Conditions for Fast IonExchange Chromatography of Proteins," Journal of Chromatography, 409-425 (1983).
Lisa D. Cabrita et al., "A Practical Guide to Protein Expression and Refolding from Inclusion Bodies," Biotech. Annual Review 10:3150 (2004).
Nov. 20, 2018 Order Regarding Claim Construction, in *Amgen Inc., et al.* v. *Mylan Inc et al.*, 2:17-cv-01235 (W. D. Pa.).
Oxford Dictionary of Biochemistry and Molecular Biology (2005).
Paul K. Ng and Valerie McLaughlin, "Regeneration Studies of Anion-Exchange Chromatography Resins," BioProcess International (May 2007).
Sarah E. Bondos and Alicia Bicknell, "Detection and prevention of protein aggregation before, during, and after purification," Analytical Biochem. 316:223-224 (2003).
Summons Returned Executed, C.A. No. 1:18-cv-03347-CCC-MF (D.N.J. Served Mar. 12, 2018).
Takao Yamada et al., "Importance of Disulfide Linkage for Constructing the Biologically Active Human Interleukin-2," Archives of Biochemistry and Biophysics, 257:194-199 (1987).
Tara M. Mezzasalma et al. "Enhancing Recombinant Protein Quality and Yield by Protein Stability Profiling, " Journal of Biomolecular Screening, 12: 418-428 (2007).
U.S. Appl. No. 12/822,990, filed Jan. 9, 2014 Amendment.
U.S. Appl. No. 12/822,990, filed Jun. 24, 2010 Claims.
U.S. Appl. No. 14/599,336, filed Jan. 16, 2015 Claims.
U.S. Appl. No. 14/599,336, filed Mar. 1, 2016 Amendment, Claims, and Arguments.
U.S. Appl. No. 14/599,336, filed Mar. 1, 2016 Information Disclosure Statement.
U.S. Appl. No. 14/599,336, filed Oct. 2, 2015 NonFinal Rejection.
U.S. Appl. No. 14/599,336, filed Sep. 1, 2016 NonFinal Rejection.
Darby et al., "Folding proteins," Nature, 344, pp. 715-716 (Apr. 19, 1990).
Information Disclosure Statement, U.S. Appl. No. 12/820,087 (now Patent No. 8,952, 138), filed Sep. 20, 2012.
Acknowledgement of consideration of references, U.S. Appl. No. 12/820,087 (now Patent No. 8,952,138), Jan. 9, 2012.
Declaration of Jared Pollack [filed in support of Amgens Motion to Exclude, attached as an exhibit to Amgens Motion to Exclude, filed in support of Amgens Opposition to Apotexs Motion to Exclude, and attached as an exhibit to Amgens Motion to Submit Supplemental Information].
Declaration of Wayne Ginoza [filed in support of Amgens Motion to Exclude, attached as an exhibit to Amgens Motion to Exclude, filed in support of.
Deposition transcript of Dr. Richard C. Willson, Aug. 9, 2017.
Deposition transcript of Dr. Roger Hart, Aug. 3, 2017.
Docket report for *Amgen Inc et al.* v. *Apotex Inc et al.*, Case No. 0:15-cv-61631-JIC, as of Oct. 20, 2017.
Email from Petitioners Counsel, Robinson revisions to testimony, May 18, 2017.
Information Disclosure Statement, U.S. Appl. No. 12/820,087 (now Patent No. 8,952, 138), filed Oct. 20, 2010.
Information Disclosure Statement, U.S. Appl. No. 12/820,087 (now Patent No. 8,952, 138), filed Sep. 23, 2010.
IPR2016-01542 Amgens Demonstratives for Oral Argument, IPR2016-01542, Dec. 13, 2017.
IPR2016-01542 Denying Petitioners Request for Rehearing and Amending Prior Decision, May 20, 2019.
IPR2016-01542 Errata to the Aug. 3, 2017 Deposition of Dr. Roger A. Hart.
IPR2016-01542 Errata to the Aug. 9, 2017 Deposition of Dr. Richard C. Willson.
IPR2016-01542 EX2057 Schlegl 950 Application USPTO Prosecution Document List.
IPR2016-01542 Excerpt of Prosecution History of U.S. Appl. No. 11/695,950 to Schlegl, Declaration of Dr. Berkemeyer.
IPR2016-01542 Handwritten Drawing/Calculations by Dr. Willson, marked during deposition.
IPR2016-01542 Hearing Order, Dec. 4, 2017.
IPR2016-01542 Metadata for Exhibit 2022.
IPR2016-01542 Metadata for Exhibit 2024.
IPR2016-01542—Order—Conduct of the Proceedings, Aug. 31, 2017.
IPR2016-01542 Order Additional Briefing, Mar. 15, 2019.
IPR2016-01542 Patent Owners First Amended Exhibit List, Mar. 15, 2019.
IPR2016-01542 Patent Owners Motion for Observation Regarding Cross-Examination of Dr. Robinson [public], Oct. 12, 2017.
IPR2016-01542 Patent Owners Motion to Exclude [public], Oct. 12, 2017.
IPR2016-01542 Patent Owners Motion to Seal, Oct. 12, 2017.
IPR2016-01542 Patent Owners Motion to Submit Supplemental Information and Exhibits, Sep. 8, 2017.
IPR2016-01542 Patent Owners Objections to Reply Evidence, Aug. 28, 2017.
IPR2016-01542 Patent Owners Opposition to Petitioners Motion to Exclude [public], Oct. 26, 2019.
IPR2016-01542 Patent Owners Opposition to Request for Rehearing, Mar. 29, 2019.
IPR2016-01542 Patent Owners Preliminary Response, Nov. 23, 2016.
IPR2016-01542 Patent Owners Reply in Support of their Motion to Exclude, Nov. 2, 2017.
IPR2016-01542 Patent Owners Request for Oral Argument, Oct. 12, 2017.
IPR2016-01542 Patent Owners Response, May 22, 2017.
IPR2016-01542 Patent Owners Second Amended Exhibit List, Oct. 12, 2017.
IPR2016-01542 Patent Owners Supplemental Claim Construction Brief, Mar. 29, 2019.
IPR2016-01542 Patent Owners Third Amended Exhibit List, Oct. 26, 2017.
IPR2016-01542 Petitioners Brief re Meaning of non-aerobic conditions, Mar. 29, 2019.
IPR2016-01542 Petitioners Motion to Exclude, Oct. 12, 2017.
IPR2016-01542 Petitioners Motion to Seal, Aug. 21, 2019.
IPR2016-01542 Petitioners Motion to Seal, Oct. 26, 2017.
IPR2016-01542 Petitioners Objections to Evidence Submitted by Patent Owner, May 30, 2017.
IPR2016-01542 Petitioners Opp to Patent Owners Motion to Exclude, Oct. 26, 2017.
IPR2016-01542 Petitioners Opposition to Patent Owners Motion to Submit Supplemental Information, Sep. 15, 2017.
IPR2016-01542 Petitioners Oral Argument Demonstratives Nov. 2, 2017.
IPR2016-01542 Petitioners Reply In Support of Motion to Exclude, Nov. 2, 2017.
IPR2016-01542 Petitioners Reply to Patent Owner Response—REDACTED, Aug. 21, 2017.
IPR2016-01542 Petitioners Request for Oral Argument, Oct. 12, 2017.
IPR2016-01542 Petitioners Response to Patent Owners Observations Regarding Cross-Examination—Redacted, Oct. 26, 2017.

US 12,269,843 B2

REFOLDING PROTEINS USING A CHEMICALLY CONTROLLED REDOX STATE

CROSS REFERENCE TO RELATED APPLICATIONS

This application is a continuation of U.S. patent application Ser. No. 15/422,327 filed on Feb. 1, 2017 (now U.S. Pat. No. 9,856,287 issued on Feb. 1, 2018), and a continuation of U.S. application Ser. No. 14/793,590 filed on Jul. 7, 2015, which is a divisional of U.S. application Ser. No. 14/611,037 filed on Jan. 30, 2015, which is a divisional of U.S. application Ser. No. 12/820,087 filed on Jun. 21, 2010 (now U.S. Pat. No. 8,952,138 issued on Feb. 10, 2015) which claims benefit of U.S. Provisional Application No. 61/219,257 filed on Jun. 22, 2009, the entire contents of all of which are incorporated by reference herein.

FIELD OF THE INVENTION

The present invention generally relates to refolding proteins at high concentrations, and more particularly to refolding proteins in volumes at concentrations of 2.0 g/L and above.

BACKGROUND OF THE INVENTION

Recombinant proteins can be expressed in a variety of expression systems, including non-mammalian cells, such as bacteria and yeast. A difficulty associated with the expression of recombinant proteins in prokaryotic cells, such as bacteria, is the precipitation of the expressed proteins in limited-solubility intracellular precipitates typically referred to as inclusion bodies. Inclusion bodies are formed as a result of the inability of a bacterial host cell to fold recombinant proteins properly at high levels of expression and as a consequence the proteins become insoluble. This is particularly true of prokaryotic expression of large, complex or protein sequences of eukaryotic origin. Formation of incorrectly folded recombinant proteins has, to an extent, limited the commercial utility of bacterial fermentation to produce recombinant large, complex proteins, at high levels of efficiency.

Since the advent of the recombinant expression of proteins at commercially viable levels in non-mammalian expression systems such as bacteria, various methods have been developed for obtaining correctly folded proteins from bacterial inclusion bodies. These methods generally follow the procedure of expressing the protein, which typically precipitates in inclusion bodies, lysing the cells, collecting the inclusion bodies and then solubilizing the inclusion bodies in a solubilization buffer comprising a denaturant or surfactant and optionally a reductant, which unfolds the proteins and disassembles the inclusion bodies into individual protein chains with little to no structure. Subsequently, the protein chains are diluted into or washed with a refolding buffer that supports renaturation to a biologically active form. When cysteine residues are present in the primary amino acid sequence of the protein, it is often necessary to accomplish the refolding in an environment which allows correct formation of disulfide bonds (e.g., a redox system).

Typical refold concentrations for complex molecules, such as molecules comprising two or more disulfides, are less than 2.0 g/L and more typically 0.01-0.5 g/L (Rudolph & Lilie, (1996) *FASEB J.* 10:49-56). Thus, refolding large masses of a complex protein, such as an antibody, peptibody or other Fc fusion protein, at industrial production scales poses significant limitations due to the large volumes required to refold proteins, at these typical product concentration, and is a common problem facing the industry. One factor that limits the refold concentration of these types of proteins is the formation of incorrectly paired disulfide bonds, which may in turn increase the propensity for those forms of the protein to aggregate. Due to the large volumes of material and large pool sizes involved when working with industrial scale protein production, significant time, and resources can be saved by eliminating or simplifying one or more steps in the process.

While protein refolding has previously been demonstrated at higher concentrations, the proteins that were refolded were either significantly smaller in molecular weight, less complex molecules containing only one or two disulfide bonds (see, e.g., Creighton, (1974) *J. Mol. Biol.* 87:563-577). Additionally, the refolding processes for such proteins employed detergent-based refolding chemistries (see, e.g., Stockel et al., (1997) *Eur J Biochem* 248:684-691) or utilized high pressure folding strategies (St John et al., (2001) *J. Biol. Chem.* 276(50):46856-63). More complex molecules, such as antibodies, peptibodies and other large proteins, are generally not amenable to detergent refold conditions and are typically refolded in chaotropic refold solutions. These more complex molecules often have greater than two disulfide bonds, often between 8 and 24 disulfide bonds, and can be multi-chain proteins that form homo- or hetero-dimers.

Until the present disclosure, these types of complex molecules could not be refolded at high concentrations, i.e., concentrations of 2.0 g/L and higher, with any meaningful degree of efficiency on a small scale, and notably not on an industrial scale. The disclosed methods, in contrast, can be performed at high concentrations on a small or large (e.g, industrial) scale to provide properly refolded complex proteins. The ability to refold proteins at high concentrations and at large scales can translate into not only enhanced efficiency of the refold operation itself, but also represents time and cost savings by eliminating the need for additional equipment and personnel. Accordingly, a method of refolding proteins present in high concentrations could translate into higher efficiencies and cost savings to a protein production process.

BRIEF DESCRIPTION OF THE DRAWINGS

FIG. 1*a* depicts the effect of a 5 mM buffer strength; FIG. 1*b* depicts the effect of a 7.5 mM buffer strength; FIG. 1*c* depicts the effect of a 10 mM buffer strength; FIG. 1*d* depicts the effect of a 12.5 mM buffer strength; FIG. 1*e* depicts the effect of a 15 mM buffer strength and FIG. 1*f* depicts the effect of a 20 mM buffer strength.

SUMMARY OF THE INVENTION

Figure 1A:
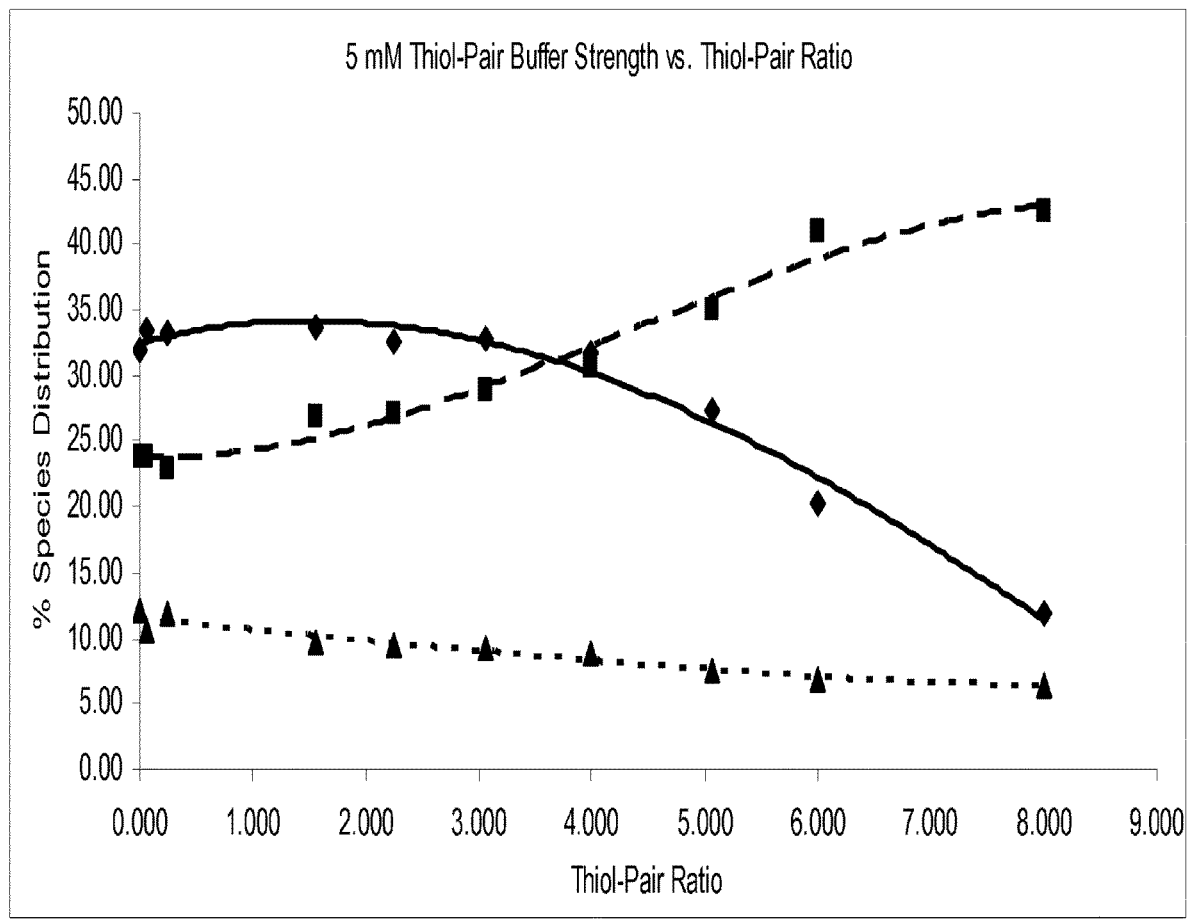
FIGS. 1*a*-1*f* is a series of plots depicting the effect of thiol-pair ratio and redox buffer strength on product-species distribution.
Figure 1B:
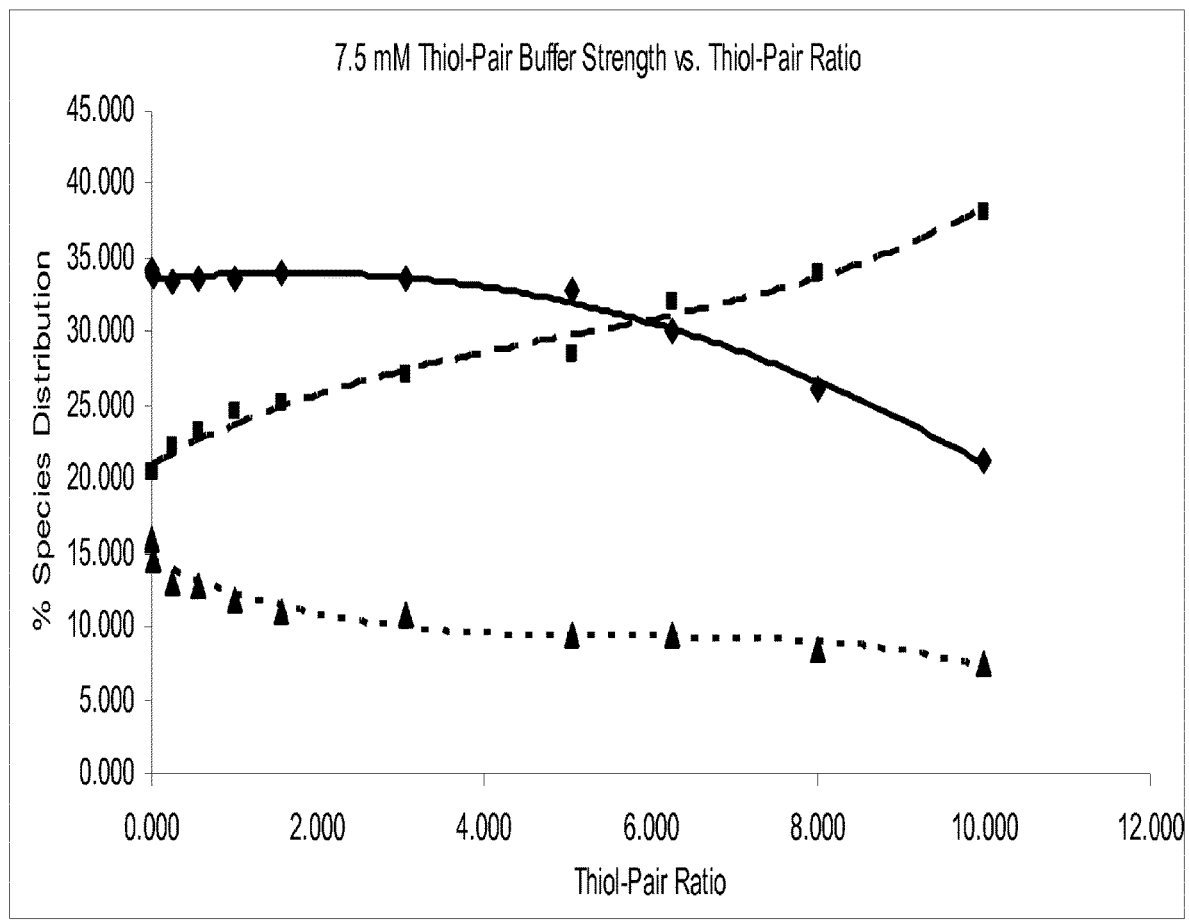
Figure 1C:
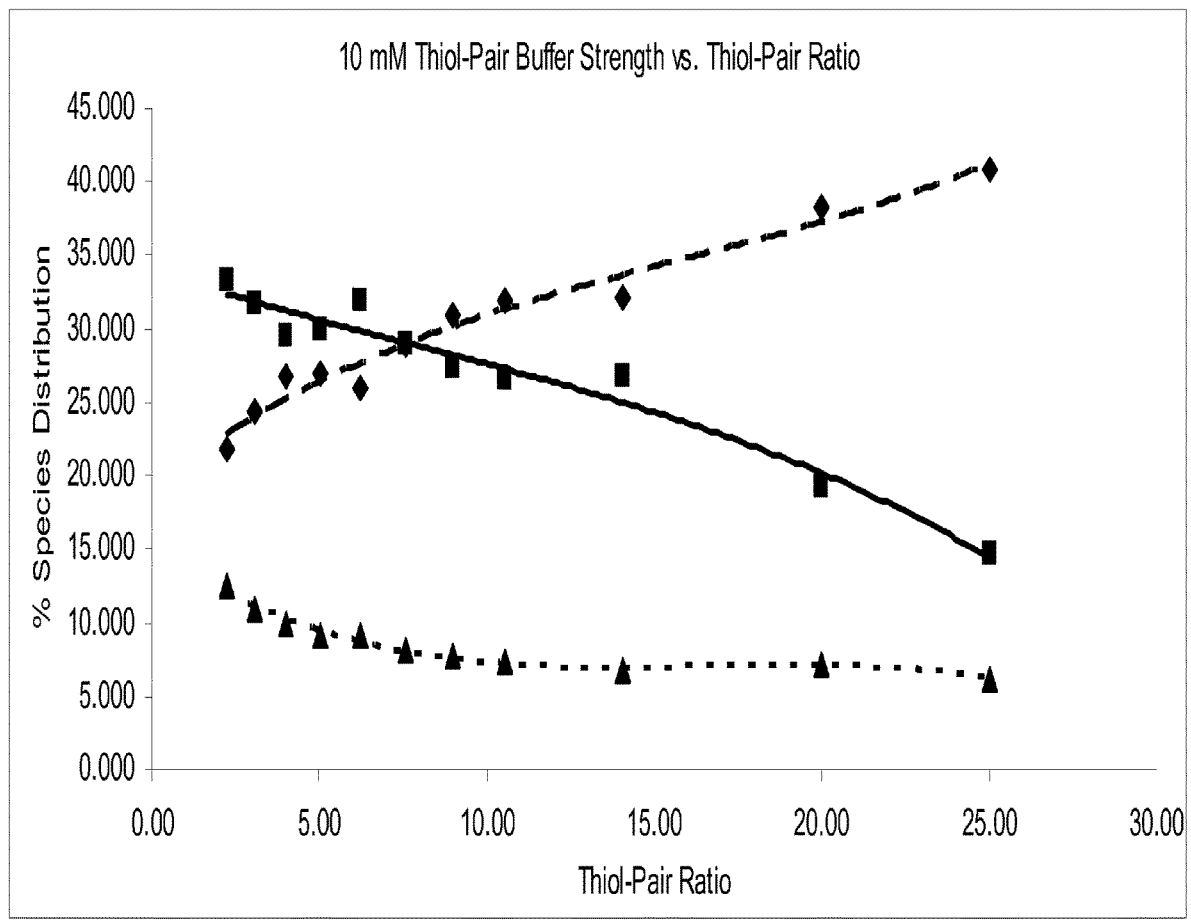
Figure 1D:
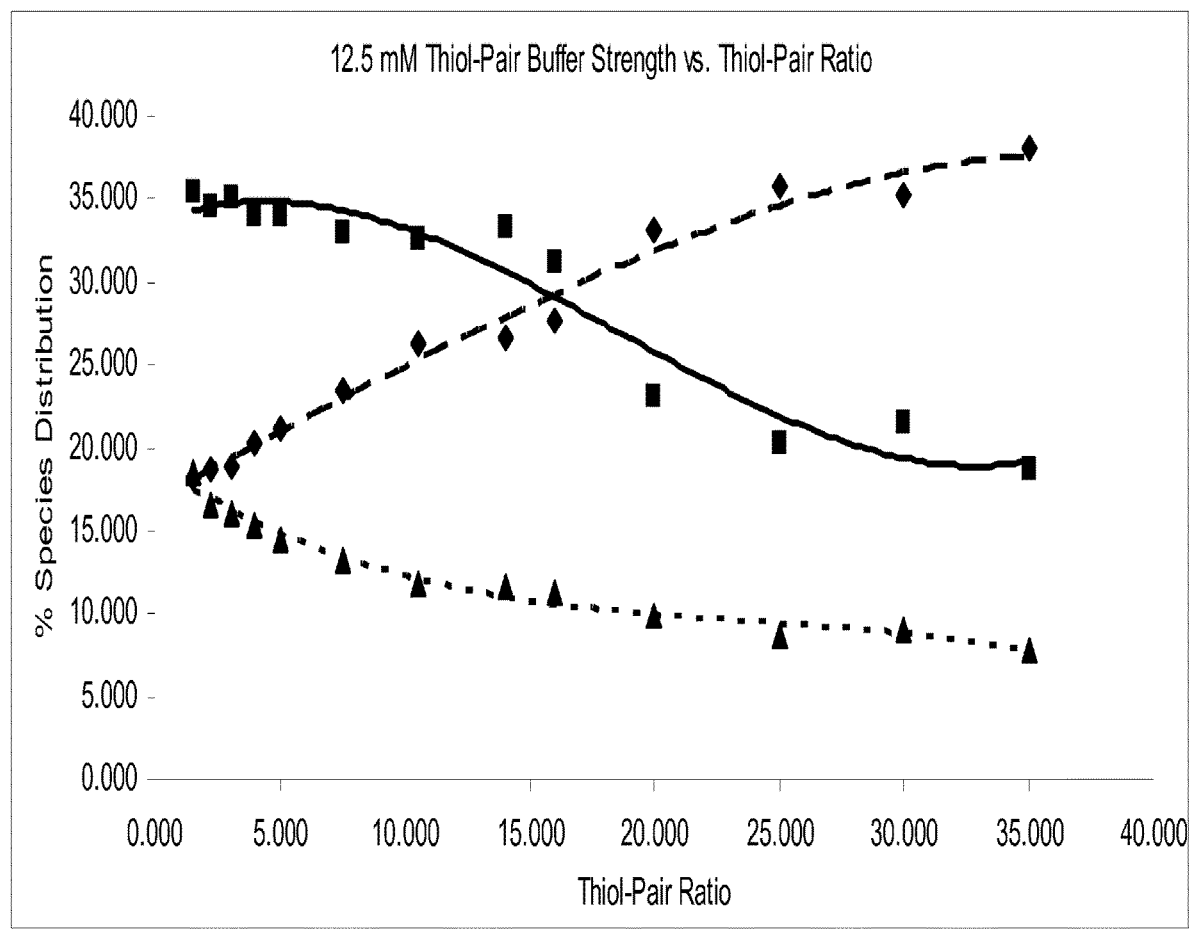
Figure 1E:
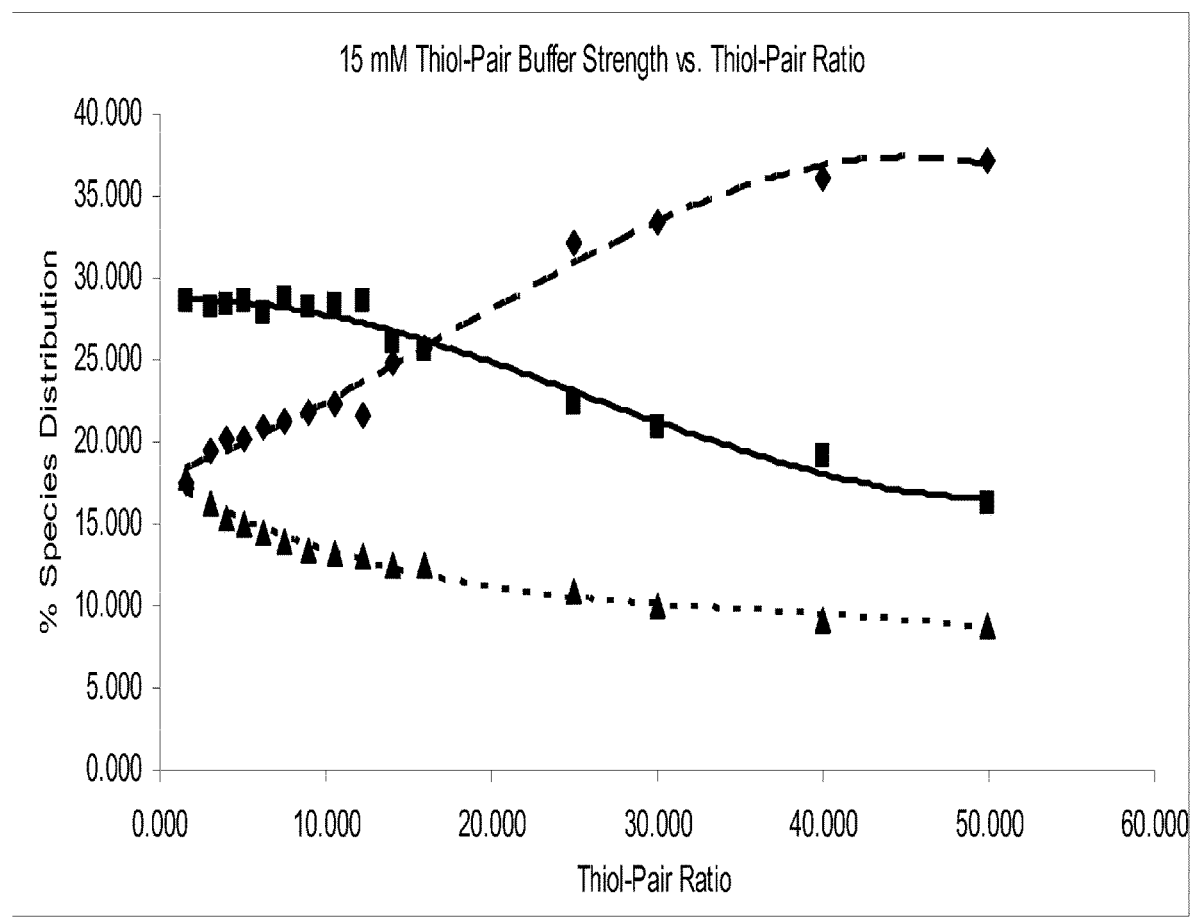
Figure 1F:
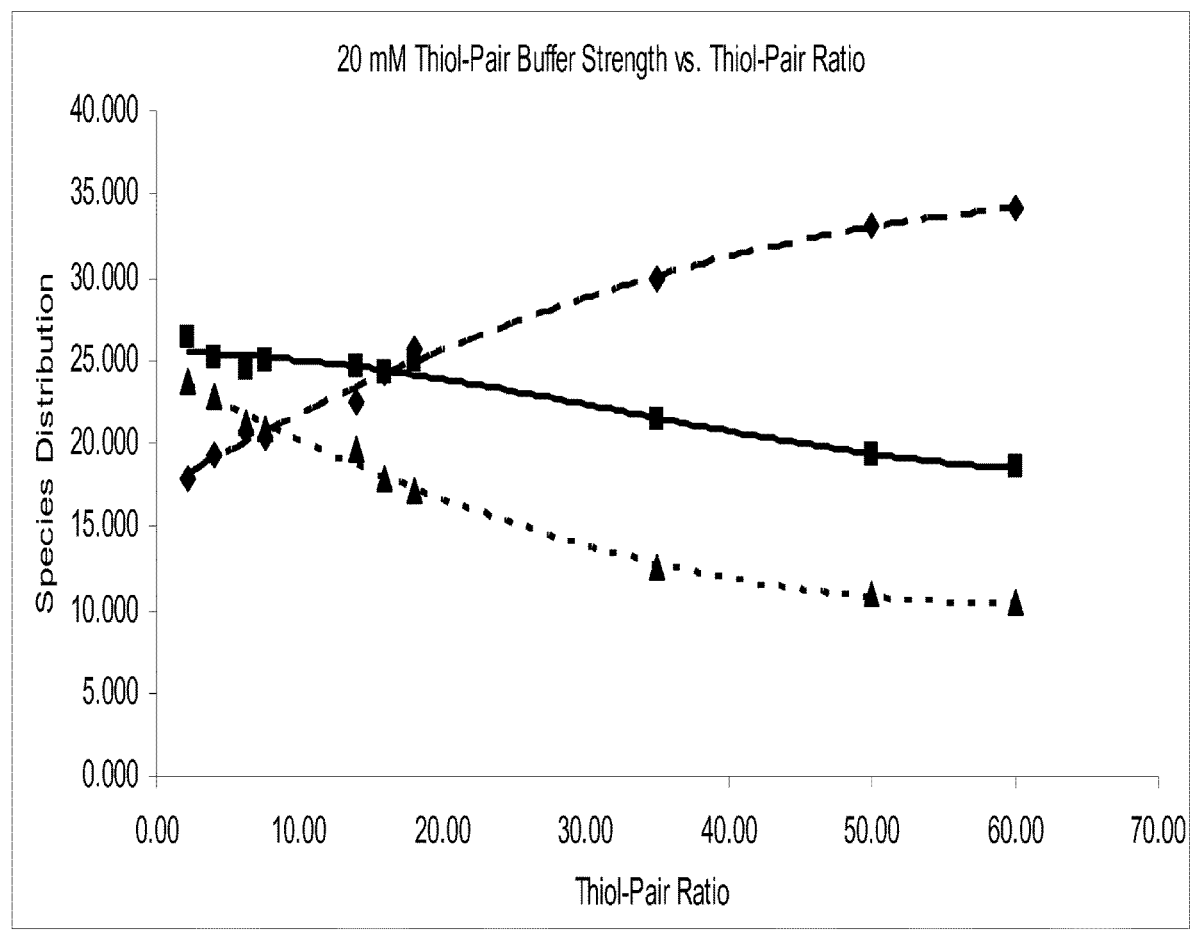

A method of refolding a protein expressed in a non-mammalian expression system and present in a volume at a concentration of 2.0 g/L or greater comprising: (a) contacting the protein with a refold buffer comprising a redox component comprising a final thiol-pair ratio having a range of 0.001 to 100 and a redox buffer strength of 2 mM or greater and one or more of: (i) a denaturant; (ii) an aggregation suppressor; and (iii) a protein stabilizer; to form a refold mixture; (b) incubating the refold mixture; and (c) isolating the protein from the refold mixture.

In various embodiments the redox component has a final thiol-pair ratio greater than or equal to 0.001 but less than or equal to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50 and a Thiol-pair buffer strength equal to or greater than 2 mM, for example greater than or equal to 2.25 mM, 2.5 mM, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength can be between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM, to form a mixture.

In one embodiment of a refold buffer, the refold buffer comprises urea, arginine-HCl, cysteine and cystamine in Tris buffer. In a further embodiment the components are present in the refold buffer in proportions described in Example 3.

In another embodiment of a refold buffer, the refold buffer comprises urea, arginine HCl, glycerol, cysteine, and cystamine in Tris buffer. In a further embodiment the components are present in the refold buffer in proportions described in Example 4.

In some embodiments, the protein is initially present in a volume in a non-native limited solubility form, such as an inclusion body. Alternatively, the protein is present in the volume in a soluble form. The protein can be a recombinant protein or it can be an endogenous protein. The protein can be a complex protein such as an antibody or a multimeric protein. In another embodiment, the protein is an Fc-protein conjugate, such as a protein fused or linked to a Fc domain.

The non-mammalian expression system can be a bacterial expression system or a yeast expression system.

The denaturant in the refold buffer can be selected from the group consisting of urea, guanidinium salts, dimethyl urea, methylurea and ethylurea. The protein stabilizer in the refold buffer can be selected from the group consisting of arginine, proline, polyethylene glycols, non-ionic surfactants, ionic surfactants, polyhydric alcohols, glycerol, sucrose, sorbitol, glucose, Tris, sodium sulfate, potassium sulfate and osmolytes. The aggregation suppressor can be selected from the group consisting of arginine, proline, polyethylene glycols, non-ionic surfactants, ionic surfactants, polyhydric alcohols, glycerol, sucrose, sorbitol, glucose, Tris, sodium sulfate, potassium sulfate and osmolytes. The thiol-pairs can comprise at least one component selected from the group consisting of glutathione-reduced, glutathione-oxidized, cysteine, cystine, cysteamine, cystamine and beta-mercaptoethanol.

In various embodiments, the purification can comprise contacting the mixture with an affinity separation matrix, such as a Protein A or Protein G resin. Alternatively, the affinity resin can be a mixed mode separation matrix or an ion exchange separation matrix. In various aspects, the incubation can be performed under aerobic conditions or under non-aerobic conditions.

DETAILED DESCRIPTION OF THE INVENTION

The relevant literature suggests that when optimizing various protein refolding operations, the refold buffer thiol-pair ratio has been purposefully varied and as a result the thiol buffer strength was unknowingly varied across a wide range of strengths (see, e.g., Lilie, Schwarz & Rudolph, (1998) *Current Opinion in Biotechnology* 9(5):497-501, and Tran-Moseman, Schauer & Clark (1999) *Protein Expression & Purification* 16(1):181-189). In one study, a relationship between the thiol pair ratio and the buffer strength was investigated for lysozyme, a simple, single-chain protein that forms a molten globule. (De Bernardez et al., (1998) *Biotechnol. Prog.* 14:47-54). The De Bernardez work described thiol concentration in terms of a model that considered only the kinetics of a one-way reaction model. However, most complex proteins are governed by reversible thermodynamic equilibria that are not as easily described (see, e.g., Darby et al., (1995) *J. Mol. Biol.* 249:463-477). More complex behavior is expected in the case of large multi-chain proteins containing many disulfide bonds, such as antibodies, peptibodies and other Fc fusion proteins. Until the present disclosure, specific relationships had not been provided for thiol buffer strength, thiol-pair ratio chemistry, and protein concentration with respect to complex proteins that related to the efficiency of protein production. Consequently, the ability to refold proteins in a highly concentrated volume has largely been an inefficient or unachievable goal, leading to bottlenecks in protein production, particularly on the industrial scale.

Prior to the present disclosure a specific controlled investigation of the independent effects of thiol-pair ratio and thiol-pair buffer strength had not been disclosed for complex proteins. As described herein, by controlling the thiol-pair buffer strength, in conjunction with thiol-pair ratio and protein concentration, the efficiency of protein folding operations can be optimized and enhanced and the refolding of proteins at high concentrations, for example 2 g/L or greater, can be achieved.

Thus, in one aspect, the present disclosure relates to the identification and control of redox thiol-pair ratio chemistries that facilitate protein refolding at high protein concentrations, such as concentrations higher than 2.0 g/L. The method can be applied to any type of protein, including simple proteins and complex proteins (e.g., proteins comprising 2-23 disulfide bonds or greater than 250 amino acid residues, or having a MW of greater than 20,000 daltons), including proteins comprising a Fc domain, such as antibodies, peptibodies and other Fc fusion proteins, and can be performed on a laboratory scale (typically milliliter or liter scale), a pilot plant scale (typically hundreds of liters) or an industrial scale (typically thousands of liters). Examples of complex molecules known as peptibodies, and other Fc fusions, are described in U.S. Pat. Nos. 6,660,843, 7,138,370 and 7,511,012.

As described herein, the relationship between thiol buffer strength and redox thiol-pair ratio has been investigated and optimized in order to provide a reproducible method of refolding proteins at concentrations of 2.0 g/L and higher on a variety of scales. A mathematical formula was deduced to allow the precise calculation of the ratios and strengths of individual redox couple components to achieve matrices of buffer thiol-pair ratio and buffer thiol strength. Once this relationship was established, it was possible to systematically demonstrate that thiol buffer strength and the thiol-pair ratio interact to define the distribution of resulting product-related species in a refolding reaction.

The buffer thiol-pair ratio is, however, only one component in determining the total system thiol-pair ratio in the total reaction. Since the cysteine residues in the unfolded protein are reactants as well, the buffer thiol strength needs to vary in proportion with increases in protein concentration to achieve the optimal system thiol-pair ratio. Thus, in addition to demonstrating that buffer thiol strength interacts with the thiol-pair ratio, it has also been shown that the buffer thiol strength relates to the protein concentration in the total reaction as well. Optimization of the buffer thiol strength and the system thiol pair ratio can be tailored to a particular protein, such as a complex protein, to minimize cysteine mispairing yet still facilitate a refold at a high concentration.

I. Definitions

As used herein, the terms "a" and "an" mean one or more unless specifically indicated otherwise.

As used herein, the term "non-mammalian expression system" means a system for expressing proteins in cells derived from an organism other than a mammal, including but not limited to, prokaryotes, including bacteria such as *E. coli*, and yeast. Often a non-mammalian expression system is employed to express a recombinant protein of interest, while in other instances a protein of interest is an endogenous protein that is expressed by a non-mammalian cell. For purposes of the present disclosure, regardless of whether a protein of interest is endogenous or recombinant, if the protein is expressed in a non-mammalian cell then that cell is a "non-mammalian expression system." Similarly, a "non-mammalian cell" is a cell derived from an organism other than a mammal, examples of which include bacteria or yeast.

As used herein, the term "denaturant" means any compound having the ability to remove some or all of a protein's secondary and tertiary structure when placed in contact with the protein. The term denaturant refers to particular chemical compounds that affect denaturation, as well as solutions comprising a particular compound that affect denaturation. Examples of denaturants that can be employed in the disclosed method include, but are not limited to urea, guanidinium salts, dimethyl urea, methylurea, ethylurea and combinations thereof.

As used herein, the term "aggregation suppressor" means any compound having the ability to disrupt and decrease or eliminate interactions between two or more proteins. Examples of aggregation suppressors can include, but are not limited to, amino acids such as arginine, proline, and glycine; polyols and sugars such as glycerol, sorbitol, sucrose, and trehalose; surfactants such as, polysorbate-20, CHAPS, Triton X-100, and dodecyl maltoside; and combinations thereof.

As used herein, the term "protein stabilizer" means any compound having the ability to change a protein's reaction equilibrium state, such that the native state of the protein is improved or favored. Examples of protein stabilizers can include, but are not limited to, sugars and polyhedric alcohols such as glycerol or sorbitol; polymers such as polyethylene glycol (PEG) and α-cyclodextrin; amino acids salts such as arginine, proline, and glycine; osmolytes and certain Hoffmeister salts such as Tris, sodium sulfate and potassium sulfate; and combinations thereof.

As used herein, the terms "Fc" and "Fc region" are used interchangeably and mean a fragment of an antibody that comprises human or non-human (e.g., murine) $C_{H2}$ and $C_{H3}$ immunoglobulin domains, or which comprises two contiguous regions which are at least 90% identical to human or non-human $C_{H2}$ and $C_{H3}$ immunoglobulin domains. An Fc can but need not have the ability to interact with an Fc receptor. See, e.g., Hasemann & Capra, "Immunoglobulins: Structure and Function," in William E. Paul, ed., *Fundamental Immunology*, Second Edition, 209, 210-218 (1989), which is incorporated by reference herein in its entirety.

As used herein, the terms "protein" and "polypeptide" are used interchangeably and mean any chain of at least five naturally or non-naturally occurring amino acids linked by peptide bonds.

As used herein, the terms "isolated" and "purify" are used interchangeably and mean to reduce by 1%, 2%, 3%, 4%, 5%, 10%, 15%, 20%, 25%, 30%, 35%, 40%, 45%, 50%, 55%, 60%, 65%, 70%, 75%, 80%, 85%, 90% or 95%, or more, the amount of heterogenous elements, for example biological macromolecules such as proteins or DNA, that may be present in a sample comprising a protein of interest. The presence of heterogenous proteins can be assayed by any appropriate method including High-performance Liquid Chromatography (HPLC), gel electrophoresis and staining and/or ELISA assay. The presence of DNA and other nucleic acids can be assayed by any appropriate method including gel electrophoresis and staining and/or assays employing polymerase chain reaction.

As used herein, the term "complex molecule" means any protein that is (a) larger than 20,000 MW, or comprises greater than 250 amino acid residues, and (b) comprises two or more disulfide bonds in its native form. A complex molecule can, but need not, form multimers. Examples of complex molecules include but are not limited to, antibodies, peptibodies and other chimeric molecules comprising an Fc domain and other large proteins. Examples of complex molecules known as peptibodies, and other Fc fusions, are described in U.S. Pat. Nos. 6,660,843, 7,138,370 and 7,511,012.

As used herein, the term "peptibody" refers to a polypeptide comprising one or more bioactive peptides joined together, optionally via linkers, with an Fc domain. See U.S. Pat. Nos. 6,660,843, 7,138,370 and 7,511,012 for examples of peptibodies.

As used herein, the term "refolding" means a process of reintroducing secondary and tertiary structure to a protein that has had some or all of its native secondary or tertiary structure removed, either in vitro or in vivo, e.g., as a result of expression conditions or intentional denaturation and/or reduction. Thus, a refolded protein is a protein that has had some or all of its native secondary or tertiary structure reintroduced.

As used herein, the term "buffer thiol-pair ratio" is defined by the relationship of the reduced and oxidized redox species used in the refold buffer as defined in Equation 1:

$$\text{Definition of Buffer Thiol-Pair Ratio } (TPR)$$

$$\text{Buffer } TPR = \frac{[\text{reductant}]^2}{[\text{oxidant}]} = \frac{[\text{cysteine}]^2}{[\text{cystamine}]}. \qquad \text{Equation 1}$$

As used herein, the terms "Buffer Thiol Strength", "Thiol-Pair Buffer Strength", and "Thiol-pair Strength" are used interchangeably and are defined in Equation 2, namely as the total mono-equivalent thiol concentration, wherein the total concentration is the sum of the reduced species and twice the concentration of the oxidized species.
Equation 2.
Definition of Buffer Thiol-Pair Buffer Strength/Thiol Buffer Strength (BS)

Thiol-Pair Buffer Strength=2[oxidant]+[reductant]=2[cystamine]+[cysteine]

The relationship between the thiol-pair ratio and thiol-pair buffer strength is described in equations 3 and 4.
Equation 3.
Calculation of the Reduced Redox Species with Regard to a Defined Redox Buffer Strength (BS) and Buffer Redox Potential $$\text{Concentration of Reduced Redox Component} = \frac{\left(\sqrt{bufferTPR^2 + 8*bufferTPR*BS}\right) - bufferTPR}{4}$$

Equation 4.
Calculation of the Oxidized Redox Species with Regard to a Defined Redox Buffer Strength (BS) and Buffer Redox Potential $$\text{Concentration of Oxidized Redox Component} = \frac{(\text{Concentration of Reduced Redox Component})^2}{TPR}$$

As used herein, the term "redox component" means any thiol-reactive chemical or solution comprising such a chemical that facilitates a reversible thiol exchange with another thiol or the cysteine residues of a protein. Examples of such compounds include, but are not limited to, glutathione-reduced, glutathione-oxidized, cysteine, cystine, cysteamine, cystamine, beta-mercaptoethanol and combinations thereof.

As used herein, the term "solubilization" means a process in which salts, ions, denaturants, detergents, reductants and/or other organic molecules are added to a solution comprising a protein of interest, thereby removing some or all of a protein's secondary and/or tertiary structure and dissolving the protein into the solvent. This process can include the use of elevated temperatures, typically 10-50° C., but more typically 15-25° C., and/or alkaline pH, such as pH 7-12. Solubilization can also be accomplished by the addition of acids, such as 70% formic acid (see, e.g., Cowley & Mackin (1997) *FEBS Lett* 402:124-130).

A "solubilized protein" is a protein in which some or all of the protein's secondary and/or tertiary structure has been removed.

A "solublization pool" is a volume of solution comprising a solubilized protein of interest as well as the salts, ions, denaturants, detergents, reductants and/or other organic molecules selected to solubilize the protein.

As used herein, the term "non-aerobic condition" means any reaction or incubation condition that is performed without the intentional aeration of the mixture by mechanical or chemical means. Under non-aerobic conditions oxygen can be present, as long as it is naturally present and was not introduced into the system with the intention of adding oxygen to the system. Non-aerobic conditions can be achieved by, for example, limiting oxygen transfer to a reaction solution by limiting headspace pressure, the absence of, or limited exposure to, air or oxygen contained in the holding vessel, air or oxygen overlay, the lack of special accommodations to account for mass transfer during process scaling, or the absence of gas sparging or mixing to encourage the presence of oxygen in the reaction system. Non-aerobic conditions can also be achieved by intentionally limiting or removing oxygen from the system via chemical treatment, headspace overlays or pressurization with inert gases or vacuums, or by sparging with gases such as argon or nitrogen, results in the reduction of oxygen concentration in the reaction mixture.

As used herein, the terms "non-native" and "non-native form" are used interchangeably and when used in the context of a protein of interest, such as a protein comprising a Fc domain, mean that the protein lacks at least one formed structure attribute found in a form of the protein that is biologically active in an appropriate in vivo or in vitro assay designed to assess the protein's biological activity. Examples of structural features that can be lacking in a non-native form of a protein can include, but are not limited to, a disulfide bond, quaternary structure, disrupted secondary or tertiary structure or a state that makes the protein biologically inactive in an appropriate assay. A protein in a non-native form can but need not form aggregates.

As used herein, the term "non-native limited solubility form" when used in the context of a protein of interest, such as a protein comprising a Fc domain, means any form or state in which the protein lacks at least one formed structural feature found in a form of the protein that (a) is biologically active in an appropriate in vivo or in vitro assay designed to assess the protein's biological activity and/or (b) forms aggregates that require treatment, such as chemical treatment, to become soluble. The term specifically includes proteins existing in inclusion bodies, such as those sometimes found when a recombinant protein is expressed in a non-mammalian expression system.

II. Theory

Refolding microbial-derived molecules present in a pool at concentrations of 2.0 g/L or higher is advantageous for a variety of reasons, primarily because of the associated reduction in reaction volumes and increases in process throughput. From a process scaling standpoint, it is advantageous to refold under conditions that do not require aerobic conditions; such conditions can be achieved, for example, by constant or intermittent sparging, the implementation of air or oxygen headspace overlays, by pressurizing the headspace, or by employing high efficiency mixing. Since the oxygen concentration in the system is related to mass transfer, the scaling of the refold reaction becomes considerably more difficult as factors such as tank geometry, volume, and mixing change. Furthermore, oxygen may not be a direct reactant in the formation of disulfide bonds in the protein, making a direct link to the mass transfer coefficient unlikely. This further complicates scaling of the reaction. Therefore, non-aerobic, chemically controlled redox systems are preferred for refolding proteins. Examples of such conditions are provided herein.

The optimal refold chemistry for a given protein represents a careful balance that maximizes the folded/oxidized state while minimizing undesirable product species, such as aggregates, unformed disulfide bridges (e.g., reduced cysteine pairs), incorrect disulfide pairings (which can lead to misfolds), oxidized amino acid residues, deamidated amino acid residues, incorrect secondary structure, and product-related adducts (e.g., cysteine or cysteamine adducts). One factor that is important in achieving this balance is the redox-state of the refold system. The redox-state is affected by many factors, including, but not limited to, the number of cysteine residues contained in the protein, the ratio and concentration of the redox couple chemicals in the refold solution (e.g., cysteine, cystine, cystamine, cysteamine, glutathione-reduced and glutathione-oxidized), the concentration of reductant carried over from the solubilization buffer (e.g., DTT, glutathione and beta-mercaptoethanol), the level of heavy metals in the mixture, and the concentration of oxygen in the solution.

Thiol-pair ratio and thiol-pair buffer strength are defined in Equations 1 and 2, infra, using cysteine and cystamine as an example reductant and oxidant, respectively. These quantities, coupled with protein concentration and reductant carry-over from the solubilization, can be factors in achieving a balance between the thiol-pair ratio and the thiol-pair buffer strength.

Turning to FIGS. 1a-1f, the effect of thiol-pair ratio and thiol buffer strength on the distribution of product-related species, as visualized by reversed phase-HPLC analysis, for a complex dimeric protein. In FIGS. 1a-1f, the dotted lines represent protein species with oxidized amino acid residues, single chain species, and stable mixed disulfide intermediates, the dashed lines represent mis-paired or incorrectly formed disulfide protein species and protein species with partially unformed disulfide linkages. The solid lines represent properly folded protein species. FIGS. 1a-1f demonstrate that at a constant 6 g/L protein concentration, as the thiol-pair buffer strength is increased, the thiol-pair ratio required to achieve a comparable species distribution must also increase. For example, as shown in FIGS. 1a-1f, if the buffer strength is increased to 10 mM, from 5 mM, the balanced thiol-pair ratio would be about 2-fold higher, to achieve a comparable species distribution. This is largely due to increased buffering of the reductant carried over from the solubilization, on the total system thiol-pair ratio. At lower redox buffer strengths, the overall system becomes much more difficult to control. The protein concentration and number of cysteines contained in the protein sequence also relate to the minimum required thiol-pair buffer strength required to control the system. Below a certain point, which will vary from protein to protein, the protein thiol concentration can overwhelm the redox couple chemistry and lead to irreproducible results.

In the results depicted in FIGS. 1a-1f, when the thiol-pair ratio of the refolding solution is intentionally set to be more reducing, the resultant product distribution shifts to produce more of the reduced product species (dashed lines). When the Thiol-Pair Ratio of the refolding solution is intentionally set to be lower, or more oxidizing, the resultant product distribution shifts to produce more oxidized residues, single chain forms, and stable mixed disulfide intermediate species (dotted lines). The ability to select an optimal Thiol-Pair Ratio and Thiol-pair Buffer Strength allows for the optimization of the yield of a desired folded protein form. This optimized yield can be achieved by maximizing the mass or yield of desired folded protein species in the refolding pool or by purposefully shifting the resultant undesired product-related species to a form that is most readily removed in the subsequent purification steps and thusly leads to an overall benefit to process yield or purity.

Optimization of the redox component Thiol-pair Ratios and Thiol-pair Buffer Strengths can be performed for each protein. A matrix or series of multifactorial matrices can be evaluated to optimize the refolding reaction for conditions that optimize yield and distributions of desired species. An optimization screen can be set up to systematically evaluate redox chemistries, Thiol-pair ratios, Thiol-pair Buffer Strengths, incubation times, protein concentration and pH in a full or partial factorial matrix, with each component varied over a range of at least three concentration or pH levels with all other parameters kept constant. The completed reactions can be evaluated by RP-HPLC and SE-HPLC analysis for yield and product quality using standard multivariate statistical tools.

III. Method of Refolding a Protein Expressed in a Non-mammalian Expression System and Present in a Volume at a Concentration of 2.0 g/L or Greater The disclosed refold method is particularly useful for refolding proteins expressed in non-mammalian expression systems. As noted herein, non-mammalian cells can be engineered to produce recombinant proteins that are expressed intracellularly in either a soluble or a completely insoluble or non-native limited solubility form. Often the cells will deposit the recombinant proteins into large insoluble or limited solubility aggregates called inclusion bodies. However, certain cell growth conditions (e.g., temperature or pH) can be modified to drive the cells to produce a recombinant protein in the form of intracellular, soluble monomers. As an alternative to producing proteins in insoluble inclusion bodies, proteins can be expressed as soluble proteins, including proteins comprising an Fc region, which can be captured directly from cell lysate by affinity chromatography. Capturing directly from lysate allows for the refolding of relatively pure protein and avoids the very intensive harvesting and separation process that is required in inclusion body processes. The refolding method, however, is not limited to samples that have been affinity purified and can be applied to any sample comprising a protein that was expressed in a non-mammalian expression system, such as a protein found in a volume of cell lysate (i.e., a protein that has not been purified in any way).

In one aspect, the present disclosure relates to a method of refolding a protein expressed in a non-mammalian expression system in a soluble form and present in a volume at a concentration of 2.0 g/L or greater, such as a protein that has been purified by affinity chromatography from the cell lysate of non-mammalian cells in which the protein was expressed. Although the volume can be derived from any stage of a protein purification process, in one example the volume is an affinity chromatography elution pool (e.g., a Protein A elution pool). In another example, the volume is situated in a process stream. The method is not confined to Fc-containing proteins, however, and can be applied to any kind of peptide or protein that is expressed in a soluble form and captured from non-mammalian-derived cell lysate. The isolated soluble protein is often released from non-mammalian cells in a reduced form and therefore can be prepared for refolding by addition of a denaturant, such as a chaotrope. Further combination with protein stabilizers, aggregation suppressors and redox components, at an optimized Thiol-pair ration and Thiol-pair Buffer Strength, allows for refolding at concentrations of 1-40 g/L, for example at concentrations of 10-20 g/L.

In one particular embodiment of the method, a protein is expressed in a non-mammalian expression system, and is released from the expressing cell by high pressure lysis. The protein is then captured from the lysate by Protein A affinity chromatography and is present in a volume at a concentration of 10 g/L or greater. The protein is then contacted with a refold buffer comprising a denaturant, an aggregation suppressor, a protein stabilizer and a redox component, wherein the redox component has a final thiol-pair ratio (as defined herein) having a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50 and a Thiol-pair buffer strength (as defined herein) equal to or greater than 2 mM, for example greater than or equal to 2.25 mM, 2.5, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM.

In another aspect, the present disclosure relates to a method of refolding a protein expressed in a non-mammalian expression system in an insoluble or limited-solubility form, such as in the form of inclusion bodies. When the protein is disposed in inclusion bodies, the inclusion bodies can be harvested from lysed cells, washed, concentrated and refolded.

Optimization of the refold buffer can be performed for each protein and each final protein concentration level using the novel method provided herein. As shown in the Examples, good results can be obtained when refolding a protein comprising an Fc region when the refold buffer contains a denaturant (e.g., urea or other chaotrope, organic solvent or strong detergent), aggregation suppressors (e.g., a mild detergent, arginine or low concentrations of PEG), protein stabilizers (e.g., glycerol, sucrose or other osmolyte, salts) and redox components (e.g., cysteine, cystamine, glutathione). The optimal thiol-pair ratio and redox buffer strength can be determined using an experimental matrix of thiol-pair ratio (which can have a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50) versus thiol-pair buffer strength (which can be greater than 2 mM, for example greater than or equal to 2.25 mM, 2.5, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM, depending on the protein concentration and the concentration of reductant used to solubilize the inclusion bodies). Conditions can be optimized using the novel methods described in Example 2.

In one particular embodiment of the method, a protein is expressed in a non-mammalian expression system and is present in a volume at a concentration of 2.0 g/L or greater. The protein is contacted with a refold buffer comprising a denaturant, an aggregation suppressor, a protein stabilizer and a redox component, wherein the redox component has a final thiol-pair ratio (as defined herein) having a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50, and a Thiol-pair buffer strength (as defined herein) equal to or greater than 2 mM, for example greater than or equal to 2.25 mM, 2.5 mM, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM. to form a mixture. A wide range of denaturant types may be employed in the refold buffer. Examples of some common denaturants that can be employed in the refold buffer include urea, guanidinium, dimethyl urea, methylurea, or ethylurea. The specific concentration of the denaturant can be determined by routine optimization, as described herein.

A wide range of protein stabilizers or aggregation suppressors can be employed in the refold buffer. Examples of some common aggregation suppressors that can be useful in the refold buffer include arginine, proline, polyethylene glycols, non-ionic surfactants, ionic surfactants, polyhydric alcohols, glycerol, sucrose, sorbitol, glucose, Tris, sodium sulfate, potassium sulfate, other osmolytes, or similar compounds. The specific concentration of the aggregation suppressor can be determined by routine optimization, as described herein.

A redox component of the refold buffer can be of any composition, with the caveat that the redox component has a final thiol-pair ratio in a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50, and a Thiol-pair buffer strength of greater than or equal to 2 mM, for example greater than or equal to 2.25 mM, 2.5, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM. Methods of identifying a suitable redox component, i.e., determining appropriate thiol-pair ratios and redox buffer strengths, are known and/or are provided herein. Examples of specific thiol pairs that can form the redox component can include one or more of reduced glutathione, oxidized glutathione, cysteine, cystine, cysteamine, cystamine, and beta-mercaptoethanol. Thus, a thiol-pair can comprise, for example, reduced glutathione and oxidized glutathione. Another example of a thiol pair is cysteine and cystamine. The redox component can be optimized as described herein.

After the protein has been contacted with a redox component having the recited thiol pair ratio and redox buffer strength to form a refold mixture, the refold mixture is then incubated for a desired period of time. The incubation can be performed under non-aerobic conditions, as defined herein. Non-aerobic conditions need not be completely free of oxygen, only that no additional oxygen other than that present in the initial system is purposefully introduced. The incubation period is variable and is selected such that a stable refold mixture can be achieved with the desired analytical properties. An incubation period can be, for example, 1 hour, 4 hours, 12 hours, 24 hours, 48 hours, 72 hours, or longer.

Due to the sensitivity of high concentration refolds to the level of oxygen present in the system and the tendency for oxygen mass transfer to be greater at small-scale, a methodology and/or apparatus can be developed to control the oxygen levels and maintain non-aerobic conditions for the incubation step. In one embodiment, the procedure can comprise the preparation, dispensing and mixing of all refold components under a blanket of inert gas, such as nitrogen or argon, to avoid entraining levels of oxygen into the reaction. This approach is particularly helpful in identifying an acceptable thiol-pair ratio. In another embodiment useful at scales of 15 liters or less, the headspace of the refold reactor containing the protein and refold buffer can be purged with an inert gas or a mixture of inert gas and air or oxygen, and the reaction vessel sealed and mixed at a low rotational speed for the duration of the incubation time.

Following the incubation, the protein is isolated from the refold mixture. The isolation can be achieved using any known protein purification method. If the protein comprises a Fc domain, for example, a Protein A column provides an appropriate method of separation of the protein from the refold excipients. In other embodiments, various column chromatography strategies can be employed and will depend on the nature of the protein being isolated. Examples include HIC, AEX, CEX and SEC chromatography. Non-chromatographic separations can also be considered, such as precipitation with a salt, acid or with a polymer such as PEG (see, e.g., US 20080214795). Another alternative method for isolating the protein from the refold components can include dialysis or diafiltration with a tangential-flow filtration system In another exemplary refolding operation, inclusion bodies obtained from a non-mammalian expression system are solubilized in the range of 10 to 100 grams of protein per liter and more typically from 20-40 g/L for approximately 10-300 min. The solubilized inclusion bodies are then diluted to achieve reduction of the denaturants and reductants in the solution to a level that allows the protein to refold. The dilution results in protein concentration in the range of 1 to 15 g/L in a refold buffer containing urea, glycerol or sucrose, arginine, and the redox pair (e.g., cysteine and cystamine). In one embodiment the final composition is 1-4 M urea, 5-40% glycerol or sucrose, 25-500 mM arginine, 0.1-10 mM cysteine and 0.1-10 mM cystamine. The solution is then mixed during incubation over a time that can span from 1 hour to 4 days.

As noted herein, the disclosed method is particularly useful for proteins expressed in bacterial expression systems, and more particularly in bacterial systems in which the protein is expressed in the form of inclusion bodies within the bacterial cell. The protein can be a complex protein, i.e., a protein that (a) is larger than 20,000 MW, or comprises greater than 250 amino acid residues, and (b) comprises two or more disulfide bonds in its native form. When the protein is expressed in an inclusion body it is likely that any disulfide bond found in the protein's native form will be misformed or not formed at all. The disclosed method is applicable to these and other forms of a protein of interest. Specific examples of proteins that can be considered for refolding using the disclosed methods include antibodies, which are traditionally very difficult to refold at high concentrations using typical refold methods due to their relatively large size and number of disulfide bonds. The method can also be employed to refold other Fc-containing molecules such as peptibodies, and more generally to refold any fusion protein comprising an Fc domain fused to another protein.

Another aspect of the disclosed method is its scalability, which allows the method to be practiced on any scale, from bench scale to industrial or commercial scale. Indeed, the disclosed method will find particular application at the commercial scale, where it can be employed to efficiently refold large quantities of protein.

The present disclosure will now be illustrated by reference to the following examples, which set forth certain embodiments. However, it should be noted that these embodiments are illustrative and are not to be construed as restricting the invention in any way.

EXAMPLES

The Examples presented herein demonstrate that thiol-pair ratio and redox buffer strength is a significant consideration in achieving an efficient refolding reaction that is insensitive to environmental influences and aeration. This insensitivity is a consideration for the ease of scaling and on an industrial or commercial scale, the transfer of the process from plant to plant.

The Examples also demonstrate that at typical refolding reaction concentrations (0.01-2.0 g/L); the sensitivity to external aeration is relatively muted. However, at concentrations of about 2 g/L and above, the sensitivity of the refold reaction to the thiol-pair ratio and redox buffer strength is increased and nearly all of the chemical components, especially the redox components, may need to be adjusted to accommodate for changes in the protein concentration in the reaction.

Example 1

Expression of Recombinant Protein

In one experiment, recombinant proteins comprising an Fc moiety were expressed in a non-mammalian expression system, namely *E coli*, and driven to form cytoplasmic deposits in the form of inclusion bodies. For each protein refolded the following procedure was followed.

After the completion of the expression phase, the cell broth was centrifuged and the liquid fraction removed, leaving the cells as a paste. The cells were resuspended in water to approximately 60% of the original volume. The cells were then lysed by means of three passes through a high pressure homogenizer. After the cells were lysed, the lysate was centrifuged in a disc-stack centrifuge to collect the protein in the solid fraction, which was expressed in a limited solubility non-native form, namely as inclusion bodies. The protein slurry was washed multiple times by repeatedly resuspending the captured solids slurry in water to between 50% and 80% of the original fermentation broth volume, mixing, and centrifugation to collect the protein in the solid fraction. The final washed inclusion bodies were captured and stored frozen.

Example 2

Identification of Refold Conditions/Redox Components

Multiple complex, microbial-derived proteins were evaluated. Each protein was solubilized in an appropriate level of guanidine and/or urea, typically at levels the equivalent of 4-6 M guanidine or 4-9 M urea, or combinations of both denaturants, which fully denatured the protein. The protein was reduced with DTT, 5-20 mM, at pH 8.5, and incubated at room temperature for approximately 1 hour.

Identification of the refold buffer was performed for each protein. A multifactorial matrix or a series of multifactorial matrices were evaluated to identify the refolding reaction for conditions that optimize yield and minimize aggregate formation. An identification screen was set up to systematically evaluate urea, arginine, glycerol and pH in a full factorial matrix, with each component varied over a range of at least three concentration or pH levels with all other parameters kept constant. The completed reactions were evaluated by RP-HPLC and SE-HPLC analysis for yield and product quality using standard multivariate statistical tools. A subset of the conditions having the desired behavior was then further evaluated in subsequent screens that evaluated a range of pH, thiol-pair ratio, thiol-pair buffer strength, and potentially further excipient levels in a factorial screen. Secondary interactions were also evaluated using standard multivariate statistical tools.

Best results, as determined by reversed-phase and size exclusion HPLC analysis, were observed using a refold buffer containing a denaturant (e.g., urea, dimethyl urea or other chaotrope at non-denaturing levels at levels between 1 and 4 M), an aggregation suppressor (e.g., arginine at levels between 5 and 500 mM), a protein stabilizer (e.g., glycerol or sucrose at levels between 5 and 40% w/v) and a redox component (e.g., cysteine or cystamine). The thiol-pair ratio and redox buffer strength were determined using an experimental matrix of thiol-pair ratio (0.1 to 100, more typically 1 to 25) versus buffer strength (typically 2 mM to 20 mM, depending on the protein concentration, the number of cysteine residues in the protein, and the concentration of reductant used to solubilize the inclusion bodies).

Individual reactions were formed with varying levels of cysteine and cystamine that would allow for a controlled matrix of thiol-pair ratio at various thiol-pair buffer strengths. The relationships were calculated using Equations 3 and 4. Each condition was screened under both aerobic and non-aerobic conditions, utilizing the techniques described herein. Optimum conditions were selected to meet a stable balance of yield, desired distribution of folding species, insensitivity to environmental oxidants (e.g., air), and insensitivity to normal variation in DTT carry-over from the solubilization step.

Example 3

High Concentration Refolding of Non-Native Soluble Protein Form Captured from Cell Lysate In one experiment, a recombinant protein comprising a plurality of polypeptides joined to an Fc moiety was expressed in *E. coli* as an intracellular soluble peptide chain, lysed from harvested and washed cells, isolated from the lysate by affinity chromatography, and then refolded at a concentration of approximately 12 g/L, as described herein.

After the completion of the expression phase, an aliquot of whole fermentation broth was centrifuged and the liquid fraction removed, leaving the cells as a paste. The cells were resuspended in water to approximately 60% of the original volume. The cells were then lysed by means of three passes through a high pressure homogenizer. After the cells were lysed, the lysate pool was mixed in the presence of air for 8-72 hours to allow for dimerization of the peptide chains. Following the dimerization process, the peptide chain of interest was isolated from the lysate pool using a Protein A affinity chromatography column. The Protein A column elution pool was mixed at a ratio of 8 parts Protein A elution material to 2 parts of a refold buffer containing urea (10 M), arginine-HCl (2.5 M), Tris at pH 8.5 (1050 mM), and cysteine (10 mM, 5 mM, or 4 mM) and cystamine (4 mM). The diluted mixture was titrated to pH 8.5 and incubated at approximately 5° C. under nitrogen until a stable pool was achieved (~24 hours.) Yields of desired product of approximately 30-80% were obtained a depending on the redox condition evaluated.

In order to emulate the non-aerobic conditions similar to those typically present in very large-scale protein production processes several steps were taken. When reaction volumes were less than approximately 15 L the refold vessel headspace was purged with nitrogen to limit the effect oxygen could have in the system. The vessel was then sealed and incubation began.

When reaction volumes were more than approximately 15 L but less than 500 L, the refold buffer was prepared and allowed to equilibrate at approximately 5° C. to achieve a stable oxygen level in the solution (typically 50% to 70% dissolved oxygen, relative to air saturation). Once the refold mixture was formed, the vessel headspace was purged with nitrogen to limit any additional effect oxygen could have in the system, the vessel was sealed and incubation period initiated.

Example 4

High Concentration Refolding From Inclusion Bodies

In one experiment, a recombinant protein comprising a biologically active peptide linked to the C-terminus of the Fc moiety of an IgG1 molecule via a linker and having a molecular weight of about 57 kDa and comprising 8 disulfide bonds, was expressed in *E. coli* as inclusion bodies, harvested, washed, concentrated, solubilized, and refolded at a concentration of 6 g/L as described herein.

An aliquot of frozen concentrated inclusion bodies were thawed to room temperature and mixed with an appropriate amount of guanidine and/or urea to generate a denaturant level equivalent to 4-6 M guanidine, which fully denatures the protein. The protein was then reduced with DTT, at 5-20 mM, at pH 8.5, and incubated at room temperature for approximately 1 hour. After the inclusion bodies were dissolved, denatured and reduced, they were diluted into a refold buffer containing urea (1-5 M), arginine-HCl (5-500 mM), glycerol (10-30% w/v), and the identified levels of cysteine and cystamine as determined by the procedure described in Example 2. The final component concentrations are 4 M urea, 150 mM arginine HCl, 20.9% (w/v) glycerol, 2.03 mM cysteine, and 2.75 mM cystamine. The level of dilution was chosen to balance the dilution of the denaturants from the solubilization, maintain the thermodynamic stability of the molecule during refolding, and maintain the highest possible protein concentration in the refold mixture. The diluted mixture was titrated to an alkaline pH (between pH 8 and pH 10) and incubated at 5° C. under non-aerobic conditions until a stable pool was achieved (12-72 hours), as determined by relevant analytical measurements. The resulting process was demonstrated to show stable scalablity from 1 L-scale to 2000 L-scale (see FIG. 3). Yields of desired product of approximately 27-35% were obtained at both scales. The distribution of product related impurities was also maintained within a tight variance (see FIG. 3).

Oxygen mass transfer at small-scale is readily achieved and should be inhibited in order to emulate the relatively poorer mass transfer observed at large-scale, where the volume of refold solution is large relative to the volume of air and surface area present at the surface of a large-scale vessel. Thus, in order to emulate the non-anaerobic conditions similar to those typically present in very large-scale protein production processes several steps were taken. When reaction volumes were less than approximately 15 L the refold buffer was sparged with nitrogen to strip oxygen from the solution, the components were dispensed under a blanket of nitrogen and once the refold mixture was formed, the vessel headspace was purged with nitrogen to limit the effect oxygen could have in the system. The vessel was then sealed and incubation began.

When reaction volumes were more than approximately 15 L but less than 500 L, the refold buffer was prepared and allowed to equilibrate at approximately 5° C. to achieve a stable oxygen level in the solution (typically 50% to 70% dissolved oxygen, relative to air saturation). Once the refold mixture was formed, the vessel headspace was purged with nitrogen to limit any addition effect oxygen could have in the system, the vessel was sealed and the incubation period was initiated.

At scales greater than 500 L the refold buffer was prepared and allowed to equilibrate at approximately 5° C. to achieve a stable oxygen level in the solution (typically 50% to 70% dissolved oxygen, relative to air saturation). Once the refold mixture was formed, the vessel was sealed and the incubation period was initiated.

The protein concentration of the refold mixture was 6 g/L, which is a four-fold enhancement over the recovery of 1.5 g/L obtained using a method other than the method described in this Example. Overall annual process productivity, in one specific manufacturing facility, was calculated to be increased by >930% due to increased volumetric efficiency in the existing facility tanks.

Example 5

Effect of Thiol-Pair Oxidation State on Disulfide Pairings

FIGS. 1a-1f demonstrate that as the thiol-pair ratio is forced to a more oxidizing state (lower thiol-pair ratio), a higher proportion of product species have oxidized amino acid residues and mixed disulfide forms. As the thiol-pair ratio is driven to a more reductive state (higher thiol-pair ratio), this results in lower levels of oxidized amino acid variant species and higher levels of product species with incorrect disulfide pairings or unformed disulfide bonds. As the overall thiol-pair buffer strength is modified, the corresponding optimal thiol-pair ratio is shifted. This effect is similar to how buffer strength modulates the sensitivity of pH to acid and base additions in a buffered solution.

An optimal balance of species was attainable. As shown in FIGS. 1a-1f, there is a clear relationship between thiol-pair buffer strength and thiol-pair ratio that can be identified to maintain the optimal species balance and thus facilitate efficient refolding of low solubility proteins. The ability to control product variant species, such as incorrectly disulfide-bonded species and misfolded species, via modulation of the thiol-pair ratio and thiol-pair buffer strength, enables efficient, effective and reliable subsequent purification processes.

Example 6

Effect of Non-aerobic Conditions on Refolding Efficiency

Figure 2:
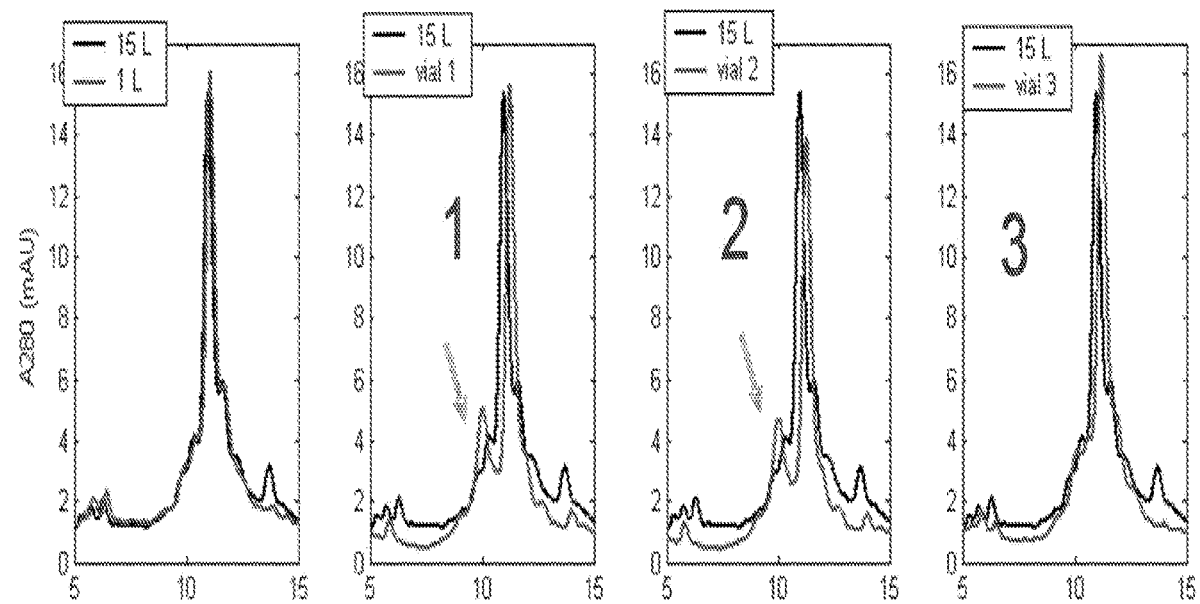
FIG. 2 is a series of plots depicting the effect of the degree of aeration on the species distribution under fixed thiol-pair ratio and thiol-pair buffer strength.
Figure 2:
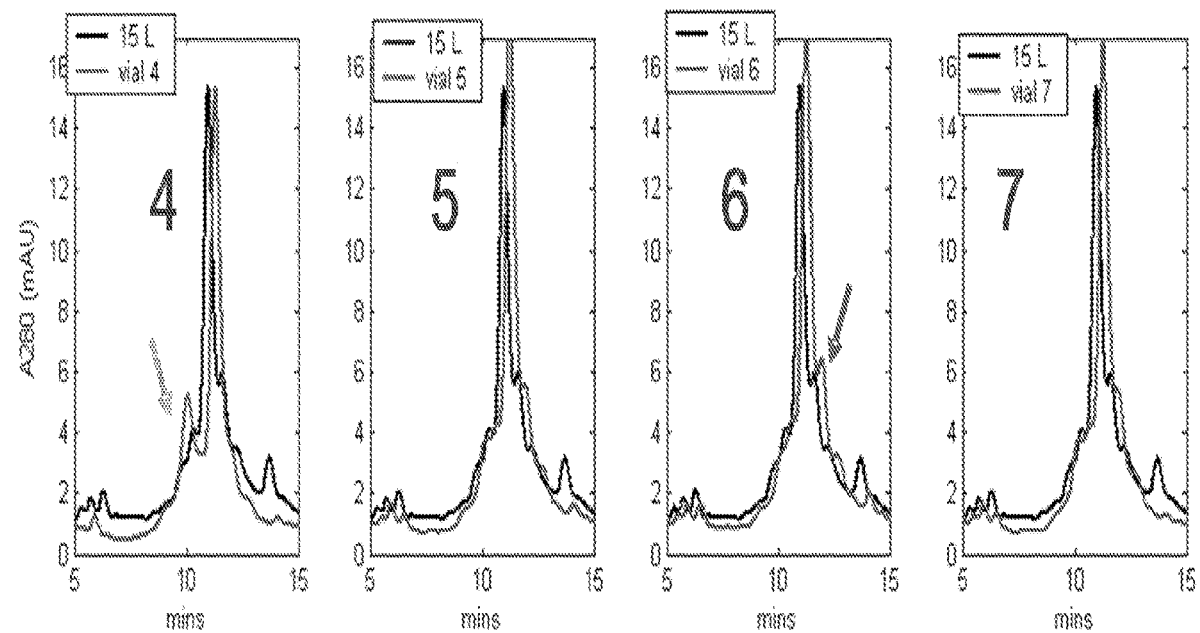
Figure 3:
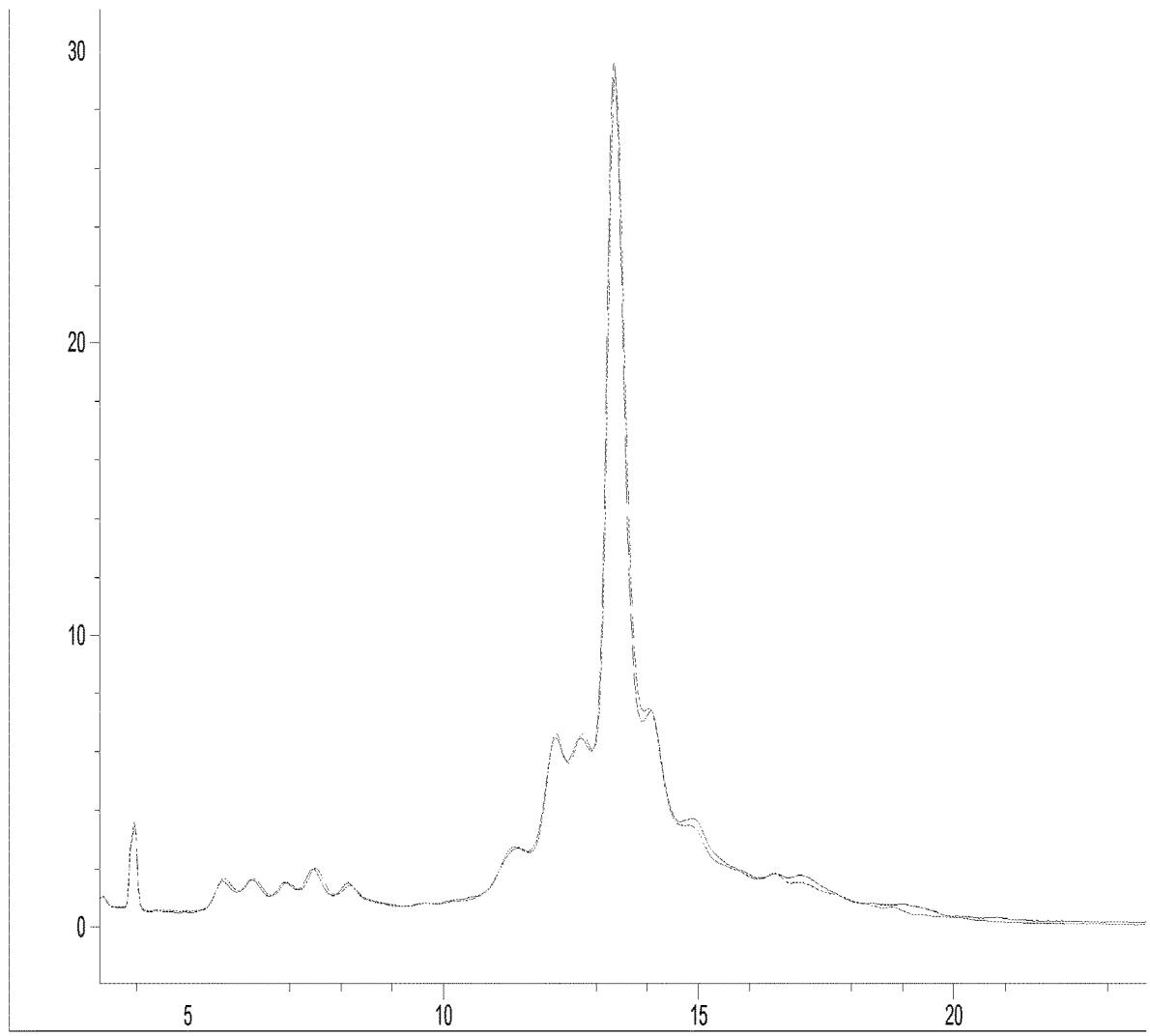
FIG. 3 is an analytical overlay of a chemically controlled, non-aerobic refold performed at 6 g/L and optimized using an embodiment of the described method performed at 1 L and 2000 L.

FIGS. 2 and 3 demonstrate that when the thiol-pair buffer strength is selected appropriately, taking into account the protein concentration and number of cysteine residues in the protein, the sensitivity to external influences, such as oxygen, is significantly reduced. This allows for a non-aerobic refolding condition that is significantly easier to transfer between scales and reactor configurations.

FIG. 2 compares the RP-HPLC analytical species distribution between a 15 L-scale refold and a 20 mL-scale refold under several environmental conditions. For Condition 1 (the trace labeled "1" in FIG. 2), the solubilization chemicals and solutions were dispensed in air and the refold mixture was incubated in air. In Condition 2 solubilization chemicals and solutions were dispensed in air and incubated under nitrogen headspace. In Conditions 3-7 solubilization chemicals and solutions were dispensed under nitrogen overlay conditions and in conditions 3, 5, 6, and 7 solubilization chemicals and solutions were incubated under nitrogen. In Condition 7, the refold solution was also stripped of nitrogen prior to combination with the solubilization solution. In Condition 4 the solubilization chemicals and solutions were incubated under ambient air conditions.

The results shown in FIG. 2 demonstrate that the conditions under which the solubilization chemicals and solutions were dispensed or incubated in the presence of air (i.e., Conditions 1, 2, and 4) do not achieve results that are comparable to the larger-scale control. In Conditions 1, 2 and 4, increased formation of oxidized species (pre-peaks) are observed. The pre-peaks are indicated by arrows in the panels for Conditions 1, 2 and 4.

FIG. 3 compares the RP-HPLC analytical results of an identified condition, achieved as described in Example 2, at 1 L-scale and 2000 L-scale. In this figure, essentially no difference in the distribution of species is detectable. Taken together, FIGS. 2 and 3 demonstrate that when aeration is carefully controlled, the small-scale refold reactions are more predictive of those expected upon scale-up of the refold reaction, facilitating the implementation of large-scale protein refolding processes.

What is claimed is:

1. A method for reproducibly obtaining proper refolding of proteins expressed in a non-mammalian expression system, the method comprising:
   (a) selecting a preparation that includes:
   at least one ingredient selected from the group consisting of a denaturant, an aggregation suppressor and a protein stabilizer;
   a concentration of oxidant; and
   a concentration of reductant;
   (b) selecting a desired yield of properly refolded proteins from a first concentration of proteins that is 1.0 g/l or greater;
   (c) determining a thiol-pair ratio of the oxidant and the reductant in the preparation based on the desired yield of properly refolded proteins;
   (d) determining a thiol-pair buffer strength for the preparation based on the determined thiol-pair ratio of (c), wherein the thiol-pair ratio and thiol-pair buffer strength are coordinated to achieve the desired yield of properly refolded proteins;
   (e) incubating the refold mixture to obtain the desired yield of properly refolded proteins;
   (f) selecting a second concentration of proteins;
   (g) adjusting, if necessary, the thiol-pair ratio for the second concentration of proteins, based on the desired yield of properly refolded proteins; and
   (h) adjusting the thiol-pair buffer strength for the second concentration of proteins until a final thiol-pair ratio is achieved, based on the adjusted thiol-pair ratio to achieve the same desired yield of properly refolded proteins for the second concentration.

2. The method of claim 1, wherein the first concentration of proteins is 2.0 g/l or greater.

3. The method of claim 1, wherein the concentration of the reductant in (a) can be calculated according to the following equation:

$$\frac{\left(\sqrt{bufferTPR^2 + 8 * bufferTPR * BS}\right) - bufferTPR}{4},$$

wherein buffer TPR is the thiol-pair ratio and BS is the thiol-pair buffer strength.

4. The method of claim 1, wherein the concentration of the oxidant in (a) can be calculated according to the following equation:

$$\frac{(\text{Concentration of reduced redox component})^2}{TPR}$$

5. The method of claim 1, wherein adjusting the thiol-pair ratio includes selecting a thiol-pair ratio for the second concentration of proteins based on the desired yield of properly refolded proteins and then adjusting the concentration of either or both the concentration of the oxidant and the concentration of the reductant.

6. The method of claim 5, wherein adjusting the concentration of either or both the concentration of the oxidant and the concentration of the reductant is by a calculation based on the selected thiol-pair ratio.

7. The method of claim 6, wherein adjusting the concentration of either or both the concentration of the oxidant and the concentration of the reductant is also by a calculation based on the adjusted thiol-pair buffer strength.

8. The method of claim 1, wherein adjusting the thiol-pair ratio for the second concentration of proteins in (g) based on the desired yield of properly refolded proteins can be determined by calculating the concentration of the reductant according to the following equation:

$$\frac{\left(\sqrt{bufferTPR^2 + 8*bufferTPR*BS}\right) - bufferTPR}{4},$$

wherein bufferTPR is the thiol-pair ratio and BS is the thiol-pair buffer strength.

9. The method of claim 8, wherein adjusting the thiol-pair buffer strength for the second concentration of proteins in (h) can be based on the adjusted thiol-pair ratio.

\* \* \* \* \*